(12) United States Patent
Favuzzi et al.

(10) Patent No.: US 8,486,714 B2
(45) Date of Patent: Jul. 16, 2013

(54) REAGENT DELIVERY SYSTEM, DISPENSING DEVICE AND CONTAINER FOR A BIOLOGICAL STAINING APPARATUS

(75) Inventors: John A Favuzzi, Santa Barbara, CA (US); Merritt M Martin, Fort Collins, CO (US); Jonathan R Sweda, Copenhagen (DK); Lauren Bland, Carpinteria, CA (US); Robert L Lathrop, San Jose, CA (US); John E Van Bosch, Ventura, CA (US); Kristopher S Buchanan, Fort Collins, CO (US)

(73) Assignee: DAKO Denmark A/S (DK)

( * ) Notice: Subject to any disclaimer, the term of this patent is extended or adjusted under 35 U.S.C. 154(b) by 1477 days.

(21) Appl. No.: 12/110,848

(22) Filed: Apr. 28, 2008

(65) Prior Publication Data

US 2009/0325309 A1    Dec. 31, 2009

Related U.S. Application Data

(63) Continuation of application No. 10/590,092, filed as application No. PCT/US2005/006383 on Feb. 28, 2005, now abandoned.

(60) Provisional application No. 60/549,889, filed on Mar. 2, 2004.

(51) Int. Cl.
*G01N 1/10* (2006.01)

(52) U.S. Cl.
USPC ............. 436/180; 422/50; 422/500; 422/501; 422/502; 422/503; 73/1.73; 73/1.74

(58) Field of Classification Search
USPC ............. 422/50, 500–503; 436/180; 73/1.73, 73/1.74
See application file for complete search history.

(56) References Cited

U.S. PATENT DOCUMENTS

| 3,960,020 A | 6/1976 | Gordon et al. |
| 4,311,667 A | 1/1982 | Gocho |

(Continued)

FOREIGN PATENT DOCUMENTS

| DE | 4313807 | 11/1993 |
| EP | 0192968 | 9/1986 |

(Continued)

OTHER PUBLICATIONS

Juroshek et al., A High-Power Automatic Network Analyzer for Measuring the RF Power Absorbed by Biological Samples in a TEM Cell, 1984, IEEE, p. 818-824.

(Continued)

*Primary Examiner* — Jyoti Nagpaul
(74) *Attorney, Agent, or Firm* — Finnegan, Henderson, Farabow, Garrett & Dunner, LLP

(57) ABSTRACT

The invention concerns reagent delivery system for an apparatus for processing of biological samples arranged on microscope slides, comprising a reagent section having one or more reagent containers; a slide section in which at least one microscope slide is arranged; a probe for dispensing a portion of reagent onto a predetermined microscope slide, and means for handling the probe. The probe comprises a continuous prove tubing element extending through a rigid probe member and connecting the probe tip to a pneumatic pressure regulation device. The reagent containers are adapted for cooperation with the probe tip. In this manner a high thoughput and a very low carry over of fluid residues is achieved since there is no assembled parts making up the inside volume of the probe in which the fluid may be retained.

31 Claims, 15 Drawing Sheets

U.S. PATENT DOCUMENTS

| | | | |
|---|---|---|---|
| 4,869,114 A | 9/1989 | Kido et al. |
| 4,967,606 A | 11/1990 | Wells et al. |
| 5,068,091 A | 11/1991 | Toya |
| 5,073,504 A | 12/1991 | Bogen |
| 5,145,646 A | 9/1992 | Tyranski |
| 5,213,764 A | 5/1993 | Kerr et al. |
| 5,287,758 A | 2/1994 | Geiss et al. |
| 5,289,385 A | 2/1994 | Grandone |
| 5,338,358 A | 8/1994 | Mizusawa et al. |
| 5,346,672 A | 9/1994 | Stapleton et al. |
| 5,355,439 A | 10/1994 | Bernstein et al. |
| 5,365,798 A | 11/1994 | Kressirer |
| 5,372,695 A | 12/1994 | Deorest |
| 5,380,486 A | 1/1995 | Anami |
| 5,399,316 A | 3/1995 | Yamada |
| 5,425,918 A | 6/1995 | Healey et al. |
| 5,439,649 A | 8/1995 | Tseung et al. |
| 5,552,087 A | 9/1996 | Zeheb et al. |
| 5,573,727 A | 11/1996 | Keefe |
| 5,578,452 A | 11/1996 | Shi et al. |
| 5,578,495 A | 11/1996 | Wilks |
| 5,595,707 A | 1/1997 | Copeland et al. |
| 5,646,049 A | 7/1997 | Tayi |
| 5,650,327 A | 7/1997 | Copeland et al. |
| 5,654,199 A | 8/1997 | Copeland et al. |
| 5,654,200 A | 8/1997 | Copeland et al. |
| 5,696,887 A | 12/1997 | Bernstein et al. |
| 5,839,091 A | 11/1998 | Rhett et al. |
| 5,896,488 A | 4/1999 | Jeong |
| 5,948,359 A | 9/1999 | Kalra et al. |
| 5,963,368 A | 10/1999 | Domanik et al. |
| 6,045,759 A | 4/2000 | Ford et al. |
| 6,063,340 A | 5/2000 | Lewis et al. |
| 6,080,363 A | 6/2000 | Takahashi et al. |
| 6,093,574 A | 7/2000 | Druyor-Sanchez et al. |
| 6,096,271 A | 8/2000 | Bogen et al. |
| 6,296,809 B1 | 10/2001 | Richards et al. |
| 6,349,264 B1 | 2/2002 | Rhett et al. |
| 6,352,861 B1 | 3/2002 | Copeland et al. |
| 6,403,036 B1 | 6/2002 | Rodgers et al. |
| 6,403,931 B1 | 6/2002 | Showalter et al. |
| 6,405,609 B1 | 6/2002 | Richards et al. |
| 6,436,349 B1 | 8/2002 | Carey et al. |
| 6,451,551 B1 | 9/2002 | Zhan et al. |
| 6,472,217 B1 | 10/2002 | Richards et al. |
| 6,495,106 B1 | 12/2002 | Kalra et al. |
| 6,498,037 B1 | 12/2002 | Caery et al. |
| 6,506,343 B1 | 1/2003 | Bodner et al. |
| 6,534,008 B1 | 3/2003 | Angros |
| 6,544,798 B1 | 4/2003 | Christensen et al. |
| 6,582,962 B1 | 6/2003 | Richards et al. |
| 6,632,598 B1 | 10/2003 | Zhang et al. |
| 6,635,225 B1 | 10/2003 | Thiem et al. |
| 6,735,531 B2 | 5/2004 | Rhett et al. |
| 6,746,851 B1 | 6/2004 | Tseung et al. |
| 6,800,249 B2 | 10/2004 | De La Torre-Bueno |
| 6,821,072 B2 | 11/2004 | Thiem et al. |
| 6,855,559 B1 | 2/2005 | Christensen et al. |
| 6,998,270 B2 * | 2/2006 | Tseung et al. ............... 436/46 |
| 7,135,992 B2 | 11/2006 | Karlsson et al. |
| 7,142,852 B2 | 11/2006 | Tell et al. |
| 7,226,788 B2 | 6/2007 | De La Torre-Bueno |
| 7,303,725 B2 | 12/2007 | Reinhardt et al. |
| 7,378,055 B2 | 5/2008 | Lemme et al. |
| 7,396,508 B1 | 7/2008 | Richards et al. |
| 7,400,983 B2 | 7/2008 | Feingold et al. |
| 7,404,927 B2 | 7/2008 | Lemme et al. |
| 2001/0010936 A1 | 8/2001 | Richards et al. |
| 2002/0001849 A1 | 1/2002 | Copeland et al. |
| 2002/0072122 A1 | 6/2002 | Copeland et al. |
| 2002/0114733 A1 | 8/2002 | Copeland et al. |
| 2003/0099573 A1 | 5/2003 | Tseung et al. |
| 2003/0100043 A1 | 5/2003 | Kalra et al. |
| 2003/0120633 A1 | 6/2003 | Torre-Bueno |
| 2004/0033163 A1 | 2/2004 | Tseung et al. |
| 2004/0219069 A1 | 11/2004 | Kalra et al. |
| 2004/0265185 A1 | 12/2004 | Kitagawa |
| 2004/0266015 A1 | 12/2004 | Favuzzi et al. |
| 2005/0038676 A1 | 2/2005 | Showalter et al. |
| 2005/0064535 A1 | 3/2005 | Favuzzi et al. |
| 2005/0124028 A1 | 6/2005 | Windeyer et al. |
| 2005/0159982 A1 | 7/2005 | Showalter et al. |
| 2006/0045806 A1 | 3/2006 | Winther et al. |
| 2006/0046298 A1 | 3/2006 | Key et al. |
| 2006/0063265 A1 | 3/2006 | Welcher et al. |
| 2006/0085140 A1 | 4/2006 | Feingold et al. |
| 2006/0088928 A1 | 4/2006 | Sweet et al. |
| 2006/0088940 A1 | 4/2006 | Feingold et al. |
| 2006/0105359 A1 | 5/2006 | Favuzzi et al. |
| 2006/0148063 A1 | 7/2006 | Favuzzi et al. |
| 2006/0178776 A1 | 8/2006 | Feingold et al. |
| 2006/0265133 A1 | 11/2006 | Cocks et al. |
| 2007/0010911 A1 | 1/2007 | Feingold et al. |
| 2007/0010912 A1 | 1/2007 | Feingold et al. |
| 2007/0196909 A1 | 8/2007 | Showalter et al. |
| 2007/0231889 A1 | 10/2007 | Angros et al. |

FOREIGN PATENT DOCUMENTS

| | | |
|---|---|---|
| EP | 0569851 | 11/1993 |
| EP | 1308731 | 5/2003 |
| JP | 03209163 A2 | 12/1991 |
| WO | WO 95/10035 | 4/1995 |
| WO | WO 97/26541 | 7/1997 |
| WO | WO 99/43434 | 9/1999 |
| WO | WO 00/02660 | 1/2000 |
| WO | WO 01/51909 | 7/2001 |
| WO | WO 01/66259 | 9/2001 |
| WO | WO 01/88500 | 11/2001 |
| WO | WO 02/056121 | 7/2002 |
| WO | WO 03/045560 | 6/2003 |
| WO | WO 03/052386 | 6/2003 |
| WO | WO 2004/074845 | 9/2004 |
| WO | WO 2004/074847 | 9/2004 |
| WO | WO 2005/031312 | 4/2005 |

OTHER PUBLICATIONS

Meldrum et al., ACAPELLA, a capillary-based submicroliter automated sample preparation system for genome analysis, 1999, IEEE, p. 39-48.

Shepard, DNA purification robotics system, 1994, IEEE. p. 424-425.

Suckau et al,, Automation of MALDI-TOF Analysis for Proteomics, 1999, IEEE, p. 1-5.

Histologic, Technical Bulletin for Histotechnology, 2001, Internet, p. 21-44.

Garrett et al., Successful techniques for supporting multidisciplinary science programs with 'ROPOS,' 1999, IEEE. p. 753-756.

* cited by examiner

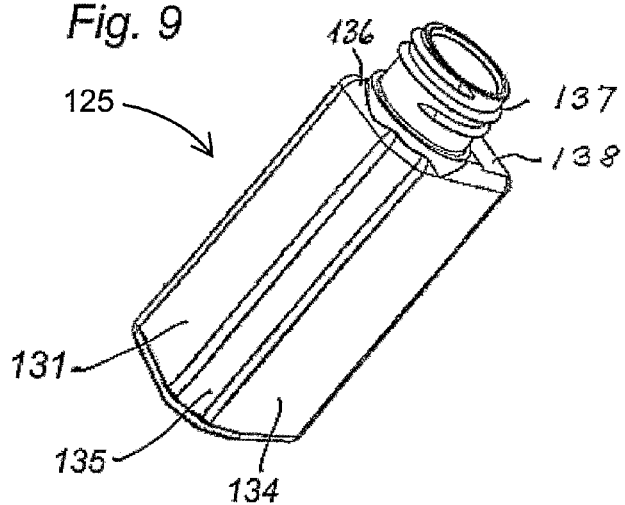
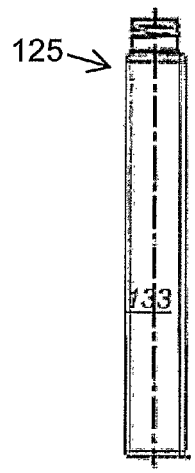
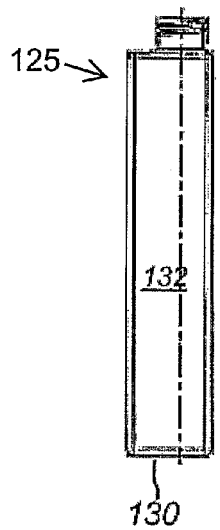
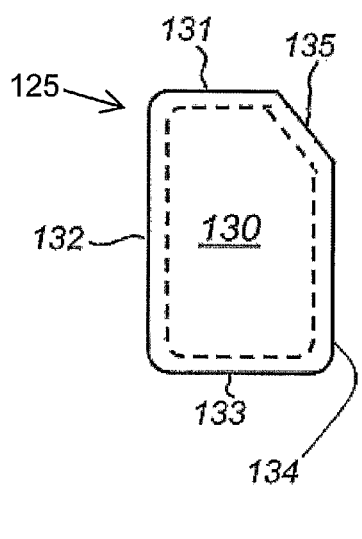

*Fig 17*
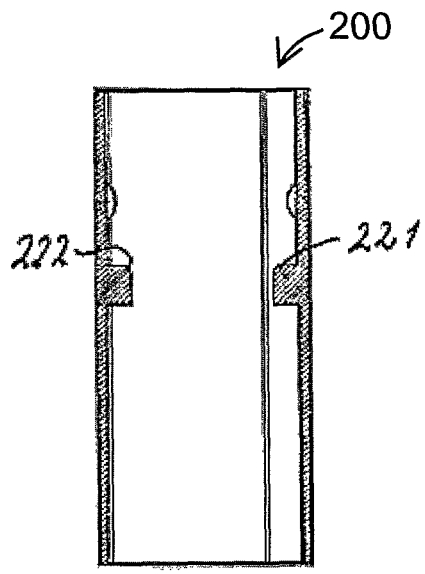
*Fig 18*
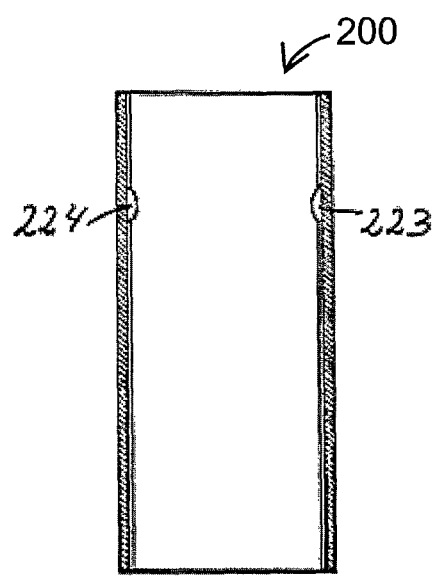
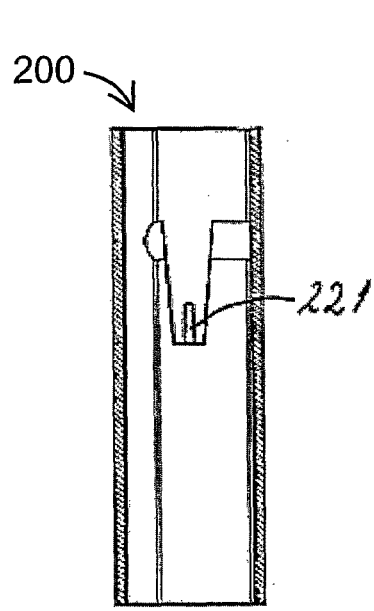
*Fig 19*
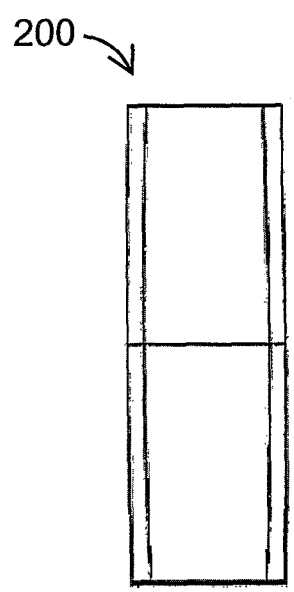
*Fig 20*

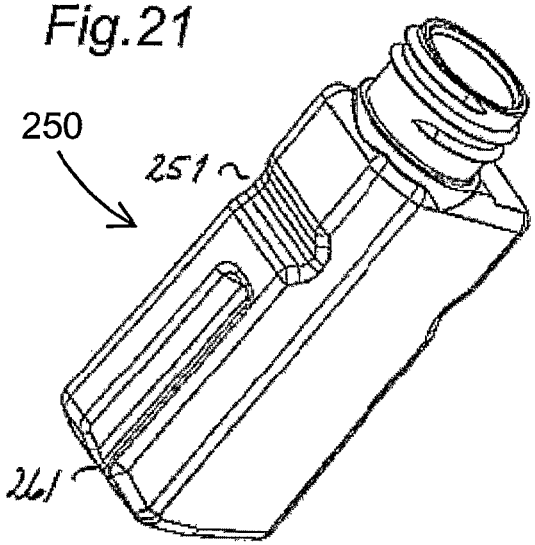
Fig.21
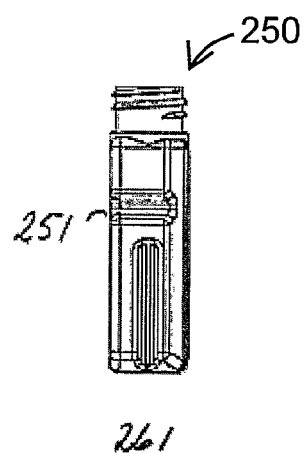
Fig.22
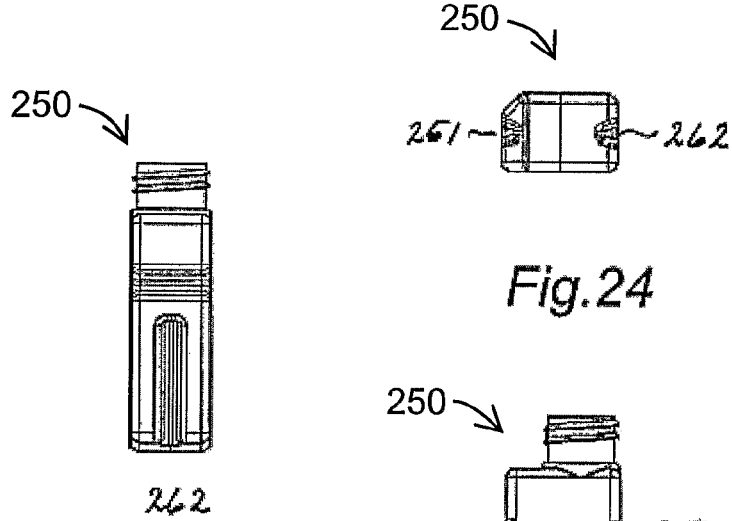
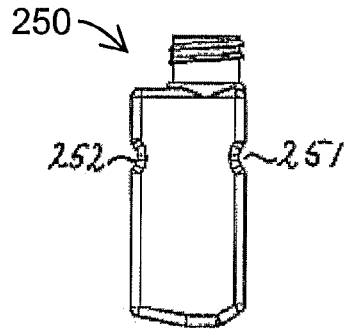
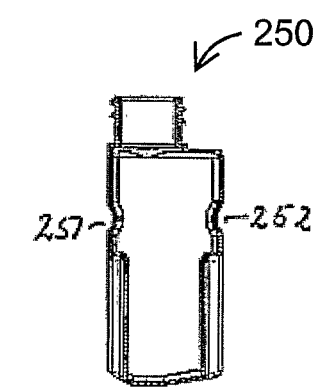
Fig.23
Fig.24
Fig.25
Fig.26

REAGENT DELIVERY SYSTEM, DISPENSING DEVICE AND CONTAINER FOR A BIOLOGICAL STAINING APPARATUS

This is a continuation of application Ser. No. 10/590,092, filed Aug. 21, 2006, now abandoned which claims priority to PCT/US2005/006383, filed Feb. 28, 2005, which claims the benefit of U.S. Provisional Application No. 60/549,889, filed Mar. 2, 2004, all of which are incorporated herein by reference.

TECHNICAL FIELD

The invention relates to a reagent delivery system in an apparatus for processing biological samples arranged on carrier elements, and a staining apparatus for processing biological samples as well as a reagent-dispensing device and a reagent container for use in such delivery systems and apparatus. The invention further relates to a method of aspirating and dispensing reagents Reagent delivery systems may be used in an automated sample processing apparatus, such as staining apparatus, for treating samples arranged on carrier means, such as microscope slides or sample tubes, located at predefined positions close to or in the apparatus by aspirating a portion of selected reagent from a station containing a plurality of reagents and thereafter dispense the reagent to a sample, e.g. a tissue, organic cells, bacteria etc., arranged on the carrier means. The invention facilitates the aspiration and dispensing of reagents.

BACKGROUND ART

Staining apparatuses for staining and treating samples by means of probes normally comprise a first station for containing one or more reagent vials; a second station for mounting slides, a probe arranged to aspirate a portion of reagent from a selected reagent vial and dispensing the reagent to a slide on which the sample is arranged and a drive means for moving the probe between the various stations.

A sample is in this application to be understood as a biological sample such as histological samples, e.g. tissue and cell specimens, including cell lines, proteins and synthetic peptides, tissues, cell preparations, blood, bodily fluids, bone marrow, cytology specimens, blood smears, thin-layer preparations, and micro arrays, and specifically biological samples on microscope slides.

The term staining is used for the end product of the process, by which certain parts of the sample may be stained, i.e. have obtained a different colour, either in the optic range or in another electromagnetic range, such as ultra violet, or the staining may be a detectable, preferably an automatically detectable, change in properties, such as fluorescent properties, magnetic properties, electrical properties or radioactive properties. To obtain the staining, the sample normally has to undergo a series of treatment steps, such as, but not limited to; washing, binding of reagents to the specific parts of the sample, activation of the reagents, etc. and each treatment step may include a plurality of individual treatments.

The vial station is a collection of a plurality of vials, at least two but often 20-60 vials or more, which may or may not be physically arranged in close proximity to each other. The term station does not indicate that the vials must be located within one, confined area; rather it indicates the existence of a plurality of vials. The probe drive means may be a robot arm with two or three degrees of freedom, such as an articulated arm or one track or a set of perpendicular tracks along which a probe retainer of the probe drive means may be displaced, wherein the probe retainer may be moved in a direction normal to the track or tracks. The skilled person may readily design other types of probe drive means, e.g. combinations of the above described. The carrier means may be provided to the apparatus in a two-dimensional array, e.g. constituted by individual rows of carrier means as discussed in the example below, or the carrier means may be provided in any manner known in the art, e.g. arranged in a carrousel or as a row of carrier means. The carrier means may also be arranged movably with respect to the probe drive means, such as in an endless row that is advanced automatically past the operating area of the probe drive means or as a two-dimensional array that may be moved in a direction perpendicular to a travel direction of the probe drive means, so that the probe may reach any carrier means by the combined movement of the probe and the array.

The carrier means are preferably arranged in groups or series on trays or the like, so that a plurality of carrier means may be removed from or situated in the apparatus simultaneously, and the apparatus preferably also comprises means for performing the intermediate storage of the carrier means with samples thereon and the removal of the carrier means from the apparatus automatically.

The operation of the staining apparatus will generally be controlled by means of control means, typically a computer having a central processing unit and one or more memory unit associated therewith, means for controlling the various operations of the apparatus by controlling step motors, solenoids, valves and/or other drive or control parts of the apparatus. The control means may have one or more data communication ports for enabling data communication with external computers by wire or wireless. The control means does not have to be physically arranged within the apparatus itself but may be a computer external to the staining apparatus and connected to the apparatus via a data transmission port thereof.

Applications to which the present invention may especially relate include immunohistochemistry, in-situ hybridization, fluorescent in-situ hybridization, special staining, and cytology, as well as potentially other chemical and biological applications.

Sample processing in immunohistochemical (IHC) applications and in other chemical and biological analyses may require one or a number of various processing sequences or protocols as part of an analysis of one or more samples. The sample processing sequences or protocols may be defined by the individual or organization requesting an analysis, such as a pathologist or histologist of a hospital, and may be further defined by the dictates of a particular analysis to be performed.

In preparation for sample analysis, a biological sample may be acquired by known sample acquisition techniques and may comprise, for example in IHC applications, tissues generally or, even in some applications, one or a plurality of isolated cells, such as in microarray samples, and may be presented on a sample carrier such as a microscope slide. Furthermore, the sample may be presented on the carrier variously and potentially in some form of preservation. As one example, a sample such as a layer or slice of skin may be preserved in formaldehyde and presented on a carrier with one or more paraffin or other chemical layers infiltrating the sample.

Immunologic and histological applications, for example, may require processing sequences or protocols that comprise steps such as deparaffinization, target retrieval, and staining, especially for in-situ hybridization (ISH) techniques. Previously, in some applications, these steps may have been performed manually, potentially creating a time-intensive protocol and necessitating personnel to be actively involved in the sample processing. Attempts have been made to automate sample processing to address the need for expedient sample processing and a less manually burdensome operation. However, such previous efforts may have not fully addressed the needs for an automated sample processing system. Previous efforts to automate sample processing may be deficient in several aspects that prevent more robust automated sample processing, such as: the lack of sufficient computer control and monitoring of sample processing; the lack of information sharing for processing protocol and processing status, especially for individual samples; the lack of diagnostic capabilities; and the lack of real-time or adaptive capabilities for multiple sample batch processing.

Past efforts at automated sample processing for samples presented on carriers such as slides, such as U.S. Pat. No. 6,352,861 to Ventana Medical Systems, Inc. and U.S. Pat. No. 5,839,091 to LabVision Corporation, have not afforded the various advantages and other combinations of features as presented herein.

U.S. Pat. No. 5,948,359 discloses an apparatus of the above mentioned type, wherein the first station comprises a vial holder for holding 40 or more vials in order to provide a wide range of different reagents adapted for different staining purposes, and thereby the possibility of automatically staining a large number of slides requiring different staining processes. In practice, it is very important that the apparatus facilitates that many different staining processes can be performed at the same time in the apparatus, because this avoids the necessity of batching samples requiring the same procedure or other treatment with reagents, and processing each batch individually.

U.S. Pat. No. 5,839,091 discloses a staining apparatus and a method of the above-mentioned kind, said apparatus comprising a reagent probe assembly for applying reagents onto a slide and wherein the probe is washed between the individual reagent applications in a wash station.

U.S. Pat. No. 6,537,818 discloses a system and method of aspirating and dispensing reagent. Also US 2003/0194349; U.S. Pat. Nos. 6,498,037; 6,436,349; 5,213,764, 4,869,114; and U.S. Pat. No. 3,960,020 show probes dispensing reagents.

An object of the present invention is to provide a reagent delivery system for a sample processing apparatus and a probe assembly therefore wherein the accuracy of dispensed volumes and the throughput is better than hereto known. Further objects of the present invention are to improve upon the known apparatuses for staining samples as well as the method for automatic staining of samples by facilitating a wider range of available processes of treatment, so as to increase the number of different staining and/or treatment processes that may be performed automatically, alternatively or additionally to provide an increased quality of some specific staining processes.

DISCLOSURE OF INVENTION

Summary of the Invention

The invention provides a reagent delivery system in an apparatus for processing biological samples arranged on carrier elements, the apparatus comprising a stationary reagent section having one or more reagent containers and a stationary staining section in which at least one carrier element is arranged; and wherein the reagent delivery system comprises a probe for aspirating a portion of reagent from a reagent container in order to dispense a predetermined amount of reagent onto a predetermined carrier element, a probe handling device for handling the probe; wherein the probe comprises a continuous probe tubing (101) extending through a rigid probe member (102) and providing fluid communication from a dispensing end (104) of said probe member to a pneumatic pressure regulation device and wherein the rigid probe member is adapted for cooperation with the closure of the reagent container. This structure enables a fast operation with a very little carry-over as the probe is easy to clean since there are no assembled parts along the inner side of the probe. Further, in order to support a fast operation, a plurality of probes such as two, three or four probes may be provided in order to allow for dispensing different reagent without washing the probe between each dispensing.

The rigid probe member may be arranged to cooperate with at least one reagent container in such manner that the probe may penetrate an opening covered by cap comprising a septum, aspirate reagent, and withdraw from the container, and wherein the septum may be adapted to regenerate as an almost tight closure of the reagent container, i.e. become substantially closed again. This is advantageous as the probe can easily get access to the content in the reagent container. No time is wasted on removing caps and, yet, the reagents will be protected against evaporation and contaminations thanks to the ability of the septum to regenerate as an almost tight closure.

In a preferred embodiment the septum comprises a plurality of sectors, e.g. four sectors, such as flaps, which are free to flex upwards or downwards, thereby allowing the aspirating end of the probe to penetrate the closure and the closure to almost regain its closed form after retraction of the probe.

Preferably, the septum comprises a plurality of sectors, e.g. four sectors, such as flaps, which originally are connected by lines of weakness, and wherein the lines of weakness will break the first time a probe is inserted into the reagent container, and, afterwards, are free to flex upwards or downwards thereby allowing the aspirating end of the probe to penetrate the closure and the closure to almost regain its closed form after retraction of the probe.

Preferably, the dispensing end of the probe is a cone in order to facilitate the penetration through the septum in the closure of the reagent container.

Preferably, a reagent container is provided with an identification, and the probe handling device comprises a robotic device also comprising a sensor element able to acquire information from the identification on the reagent container, and the robotic device is connected to a computer receiving the acquired information. Such identification enables the computer system controlling the reagent delivery in an automated stainer to obtain information about the reagent containers located in the reagent section of the apparatus. In this manner, it is possible to check that the reagent delivery system is aspirating the prescribed reagent.

The invention also provides a staining apparatus for automated processing of biological samples arranged on carrier elements, comprising a reagent section comprising one or more reagent containers; a staining section in which at least one carrier element is arranged; a reagent dispensing device for dispensing a portion of reagent onto a predetermined carrier element, a handling device for handling said reagent dispensing device; wherein the reagent dispensing device comprises a continuous probe tubing extending through a rigid probe member and providing fluid communication from a dispensing end of said probe member to a pneumatic pressure regulation device.

The pneumatic pressure regulation device may include a vacuum source with which the tubing may communicate via a valve device. Preferably said valve device is operable to provide a predetermined pressure in the tubing in order to aspirate or dispense a predetermined amount of reagent at the dispensing end of the tubing. By controlling the pressure inside the tubing, the aspiration and dispensing of fluids may be accurately controlled. By using pneumatic means for operating the probe tubing, the available reagent in the reagent containers as well as the available volume in the probe tubing may be fully exploited as reagent may be withdrawn from the reagent containers by applying vacuum to the tubing.

In a preferred embodiment, the handling device includes a holder for holding the probe member; and a robotic motion system for moving the reagent dispensing device between predetermined locations relative to the carrier element and the reagent containers. The reagent dispensing device may be moved by a computer controlled robotic system able to direct the device to a specific reagent container for aspirating a volume of reagent and to move on to a specific microscope slide to dispense the volume of reagent on the slide.

In a preferred embodiment of the probe, the internal diameter of the tubing is between 1.0 mm and 2.0 mm, preferably, between 1.2 mm and 1.8 mm and, more preferably, between 1.4 mm and 1.6 mm, such as about 1.5 mm (1/16 inch). The internal diameter is chosen so that the aspirated volume of reagent can be withheld in the tube. Further, the narrow tube allows for a plurality of aspirated volumes separated by air bubbles aspirated between each volume of reagent. Aspirating a plurality of volumes for a plurality of microscope slides is very time-saving, supporting a high through-put of the apparatus, as the probe only moves once from reagent section to the staining section with the slides.

The length of the tubing may be between 0.5 m and 2.5 m, preferably, between 1.0 m and 2.0 m and, more preferably, between 1.3 m and 1.7 m, such as about 1.5 m. The length is advantageous for the ability to aspirate a plurality of volumes of reagents. Accordingly the length support a high through-put of the apparatus In a preferred embodiment, the continuous tubing is provided with a spirally wound probe tubing section. This is advantageous for accommodation of the long thin tubing. Further the spiral section provides for the flexibility required when the probe is moved up or down. This is advantageous as the opposite end of the long tubing stays permanently connected to the pneumatic system.

In the preferred embodiment, the spirally wound probe tubing section is a coiled section. The coiled section may comprise at least one winding, and, preferably, between 5 and 30 windings, more preferably, between 10 and 25 windings, and, most preferably, between 15 and 22 windings, such as 20 windings.

The staining apparatus may comprise a washing station for cleaning the reagent-dispensing device. The valve device may further be adapted to provide a connection to a fluid source providing a wash solution or cleaning fluid for washing and or rinsing the probe tubing. Preferably the washing station comprises a receptacle (wash sump) able to accommodate a substantial portion of the dispensing end of the probe, and an outlet to waste, and the outlet to the waste may be located a distance above the bottom of the receptacle so that the wash fluid ejected from the dispensing end of the probe will wash the outer surface of the dispensing end of the probe before the wash fluid is drained to waste. Accordingly the probe can be washed in a fast and effective manner inside as well as outside in a single process. After the wash, the probe may be dried by air supplied to the tubing through the valve device. The washing fluid may be selectable from a plurality of fluids according to the tube cleaning requirements.

In a staining apparatus according to the invention, the reagent section comprises a reagent rack providing a plurality of compartments for a plurality of reagent containers or container assemblies and wherein the cross-section of a compartment cooperates with the cross-section of the container or container assembly. The cross-section may be an unsymmetrical polygon, such as a rectangle with one corner-section replaced by a slanted/oblique fifth side.

In a staining apparatus according to the invention, a top wall of a reagent container is provided with a label comprising information identifying, for instance, type of reagent, container volume size, date of delivery, date of end of use, and wherein the robot head further comprises an optical sensor, able to provide the information on the label to a computer system. These features are essential to the operation of the automated staining apparatus, in order to enable thorough control of the application of the prescribed reagent to the specified slide. A control system may include software for registering and tracking different relevant data and controlling the robotic movements and the washing action in accordance with a predetermined staining protocol transmitted to the control system.

In a preferred embodiment, an electrically conducting member of the reagent dispensing device is connected to an electronic circuit adapted for capacitive level sensing (having ability to detect the reagent level by sensing an electrical capacity, and adapted to forward information about the detected level to the computer system). Further, the computer system may be adapted to issue an order for a new delivery of the reagent if the level is below a predetermined limit.

In a preferred embodiment, wherein the computer system is connected to a plurality of staining apparatuses, and further uses the reagent dispensing device to detect the level of reagent fluid in each reagent container, a controlling program is adapted to let the robotic system with the level sensor and the optical sensor update information about the available amount of reagent in the reagent containers in the plurality of staining apparatus before starting a staining procedure, and is further adapted to recommend to an operator that a tissue slide requiring a specific reagent, be processed in a staining apparatus having a reagent container comprising the necessary volume of such specific reagent.

The invention provides a reagent dispensing device for use in a staining apparatus for processing of biological samples arranged on carrier elements, said device comprising a probe member having an aspirating and dispensing end, through which reagent may be aspirated and dispensed, and a mounting end; and wherein a continuous probe tubing is provided inside the probe member, said tubing extending from the aspirating and dispensing end through the entire probe member to pneumatic pressure regulation device. Such probe is easy to wash and carry-over is minimized as there are no assembled parts in the inner surface of the probe.

Preferably, the internal diameter of the tubing is between 1.0 mm and 2.0 mm, preferably, between 1.2 mm and 1.8 mm and, more preferably, between 1.4 mm and 1.6 mm, such as about 1.5 mm (1/16 inch). Preferably, the length of the tubing is between 0.5 m and 2.5 m, preferably, between 1.0 m and 2.0 m and, more preferably, between 1.3 m and 1.7 m, such as about 1.5 m. This allows for the probe to have an inner volume enabling the probe to contain a plurality of aspirated volumes of reagent. In this manner, the probe may transfer a plurality of reagent volumes from the reagent section to the staining section in a single movement of the probe from the reagent section to the slide section where the plurality of reagent volumes can be dispensed on a plurality of specified microscope slides. This saves considerable time. This also makes it possible to withdraw a large volume of reagent for staining a multiple of biological samples, e.g. a batch of slides. This results in a fast processing of biological samples in a staining apparatus according to the invention.

Preferably, the continuous tubing is provided with a spirally wound probe tubing section, and the spirally wound probe tubing section may be a coiled section, wherein the coiled section comprises at least one winding, preferably between 5 and 30 windings, more preferably, between 10 and 25 windings, and, most preferably, between 15 and 22 windings, such as 20 windings. This is advantageous for accommodation of the long thin tubing. Further the spiral section provides for the flexibility required when the probe is moved up or down.

In a preferred embodiment, the mounting end of the probe member includes a fitting for mounting the device to a probe holder on a probe handling device, such as a robotic head that is part of a computer controlled robotic system in a staining apparatus.

The invention further provides a reagent container for use in a reagent delivery system according to any of the claims 1-6, characterised in that the cross-section of the container is a non-symmetrical polygon. In a preferred embodiment, the cross-section of the container is a rectangle with one corner-section replaced by a slanted/oblique fifth side.

According to the invention, a reagent container may have a box-like form, comprising a bottom wall, four side walls and a top wall, and wherein one corner section is replaced by a single slanted/oblique sidewall, ensuring a specified orientation of the container when inserted into a corresponding compartment a reagent container rack, arranged to accommodate a plurality of containers in rows and columns.

According to the invention, there is provided a reagent container assembly for use in a reagent delivery system according to any of the claims 1-6, characterised by comprising a covering or shell forming an adapter, which is able to accommodate a reagent container, and further characterised in that the cross-section of the assembly is a non-symmetrical polygon. Preferably, the cross-section of the assembly as well as of the reagent container is a rectangle with one corner-section replaced by a slanted/oblique fifth side.

In a preferred embodiment, the reagent container comprises a closure comprising a plurality of sectors, e.g. 4 sectors, such as flaps, which are free to flex upwards or downwards thereby allowing the aspirating end of the reagent dispensing device to penetrate the closure and the closure to regain its closed form after retraction of the probe.

The present invention further presents a method of aspirating and dispensing reagents onto a plurality of samples on carriers (tissue slides) in an automated tissue staining apparatus having a slide section, a reagent section and a probe mounted on a robot head of a computer controlled robotic system, characterised by comprising at least one action from the group comprising beginning X-movement of a robot head; moving the robot head an appropriate distance along an X-axis for a probe wash location; ending X-movement of the robot head; beginning Y-movement of a robot head; moving the robot head an appropriate distance along an Y-axis for a probe wash location; ending Y-movement of the robot head; beginning Z-movement of a robot head; lowering a probe tip into a wash area; ending Z-movement of the robot head; switching a valve to activate a probe wash source; opening a valve to begin flow of a wash liquid from the probe wash source; washing the probe; closing a valve to end flow of a wash liquid from the probe wash source; beginning Z-movement of a robot head; raising the probe tip; ending Z-movement of the robot head; beginning X-movement of a robot head; moving a robot head an appropriate distance along an X-axis for a desired reagent container; ending X-movement of the robot head; beginning Y-movement of a robot head; moving a robot head an appropriate distance along an Y-axis for a desired reagent container; ending Y-movement of the robot head; beginning Z-movement of a robot head; lowering the probe tip over a desired reagent container; ending Z-movement of the robot head; switching a valve to utilize a reagent aspiration pressure source; opening a valve to begin access to the reagent aspiration pressure source; aspirating reagent; closing a valve to end access to the reagent aspiration pressure source; beginning Z-movement of a robot head; raising the reagent containing probe tip; ending Z-movement of the robot head; beginning X-movement of a robot head; moving a robot head an appropriate distance along an X-axis for a particular slide; ending X-movement of the robot head; beginning Y-movement of a robot head; moving a robot head an appropriate distance along an Y-axis for a particular slide; ending Y-movement of the robot head; beginning Z-movement of a robot head; lowering the reagent containing probe tip over a particular slide; ending Z-movement of the robot head; switching a valve to utilize a reagent emission pressure source; opening a valve to begin access to the reagent emission pressure source; emitting reagent; closing a valve to end access to the reagent emission pressure source; beginning Z-movement of a robot head; raising the empty probe tip; and ending Z-movement of the robot head. Accordingly, any reagent container may be accessed by the probe through a combination of movements of the robotic system—a predetermined volume of reagent or a plurality of predetermined volumes may be aspirated—and later dispensed to one or a plurality of specified slides. The method enables a very efficient and accurate schedule allowing for a high through-put of the apparatus.

Preferably, according to the method, lowering the probe tip over a desired reagent container comprises that the probe tip get in touch with a sealing top closure of the reagent container, and, further lowering the probe a further distance causes the probe to penetrate through the sealing top closure of the reagent container; thereby allowing the probe to get access to the content of the reagent container without removal of a cap and, yet, with very little or no evaporation of the reagent.

The present invention further provides a method of aspirating and dispensing reagents onto a plurality of samples on carriers (tissue slides) characterised by aspirating a plurality of predetermined volumes of a predetermined reagent, further characterised by aspirating a predetermined amount of air between each of the predetermined volumes of a reagent, in such a manner that every volume of the plurality of volumes is separated from neighboring volumes by air bubbles. In this manner, the plurality of predetermined volumes may be dispensed very accurately onto a plurality of slides.

According to this method, the probe tubing having aspirated a predefined volume of a first reagent may be removed from the first reagent container, aspirate a predetermined amount of air, forming an air gap or bubble inside the tubing, and then enter into a second reagent container and aspirate the second reagent. The air bubble separates the two reagents and the meniscus of the bubble acts as a wiper within the inner tubing wall to eliminate cross contamination between these two distinct fluids. In similar manner, a plurality of different reagents may be aspirated and separated by air during a single period in which the robotic head locates the probe over the reagent section of the stainer. Afterwards, the computer controlled robotic head can move the probe to the section with the slides, and, during the following period, dispense one or more reagents onto a single or a plurality of slides, possibly requiring different reagents.

In a preferred embodiment of the invention, the internal diameter of the tubing is 1.5 mm (1/16 inch). The small internal diameter allows for the air bubble to maintain a stable form as it moves in the tubing. Each single bubble will stay as a single entity and not break up into multiple bubbles; neither can it collapse with any other bubble. This behavior means that the amount fluid to be dispensed may be controlled accurately, even when a plurality of fluid volumes have been aspirated by the probe. The possibility of aspirating a plurality of separated volumes allows for a fast dispensing of the fluids onto one or a plurality of slides in the staining section.

BRIEF DESCRIPTION OF DRAWINGS

The invention will now be explained in further detail with reference to the enclosed drawings, showing as non-limiting examples presently preferred embodiments of the invention and wherein

FIG. 9 shows a perspective view of a 50 ml reagent container.

FIGS. 10 and 11 show side views of the same container of FIG. 9.

FIG. 12 shows a bottom view of the same container of FIG. 9.

FIG. 17 shows a cross-sectional view of the adapter along the lines A-A in FIG. 14.

FIG. 18 shows a cross-sectional view of the adapter along the lines B-B in FIG. 14.

FIG. 19 shows a cross-sectional view of the adapter along the lines C-C in FIG. 14.

FIG. 20 shows a side view of the adapter of FIG. 13.

FIG. 21 shows a perspective view of a 25 ml container.

FIGS. 22, 23 and 25 show side views of the 25 ml container of FIG. 21.

FIG. 24 shows a bottom view of the 25 ml container of FIG. 21.

FIG. 26 shows a cross-sectional view of the 25 ml container of FIG. 21.

The embodiments shown in the figures and described in details below are only to be considered as examples of an apparatus in accordance with the present invention and are not limiting the wider scope of the invention as described in the enclosed claims. In the following examples, the sample processing apparatus according to the invention is a staining apparatus.

MODES FOR CARRYING OUT THE INVENTION

DETAILED DESCRIPTION

EXAMPLE

Best Mode for Carrying Out the Invention

Figure 1:
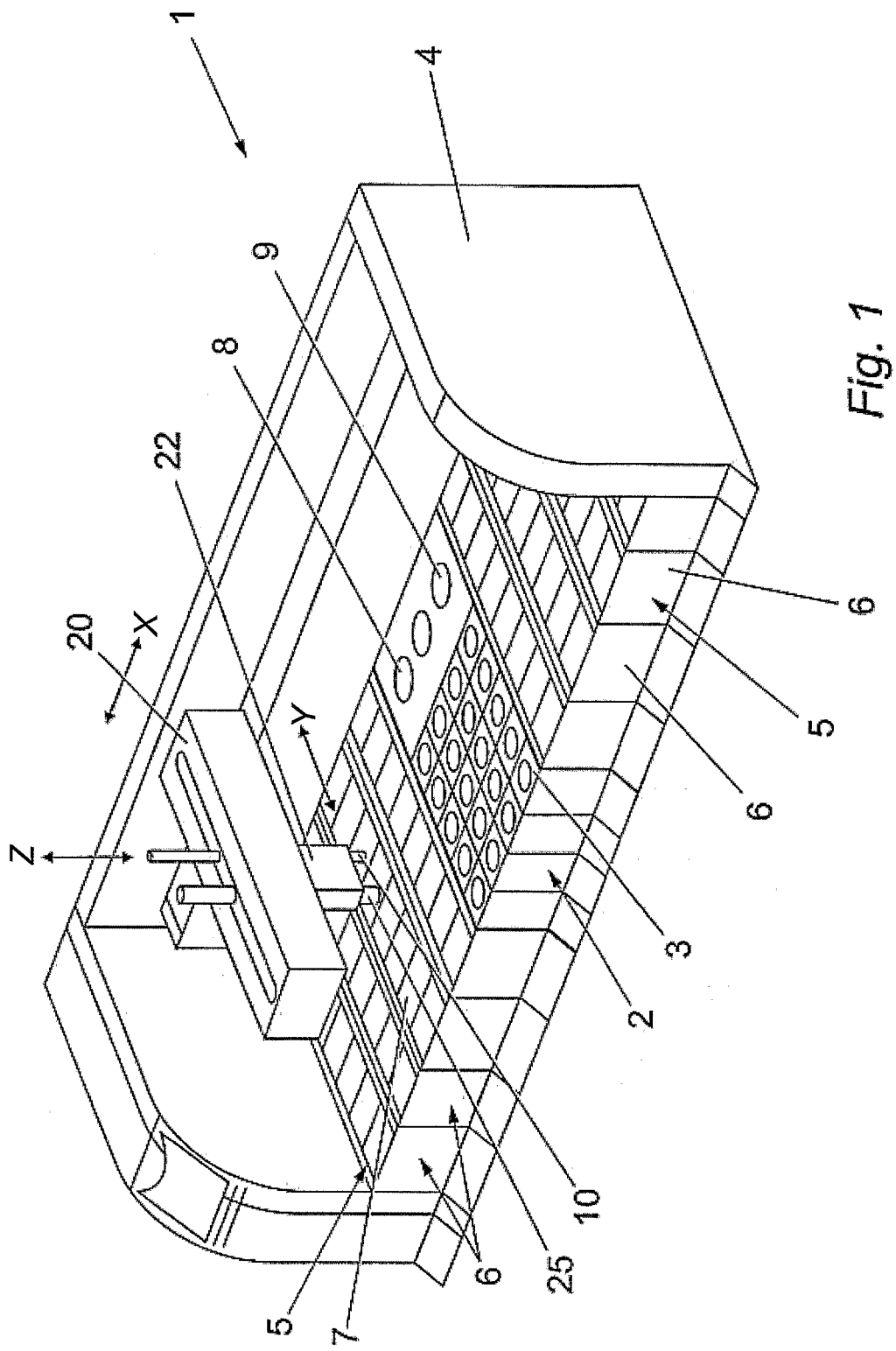
FIG. 1 is a perspective view of an embodiment of a sample processing apparatus according to the invention.
Figure 2:
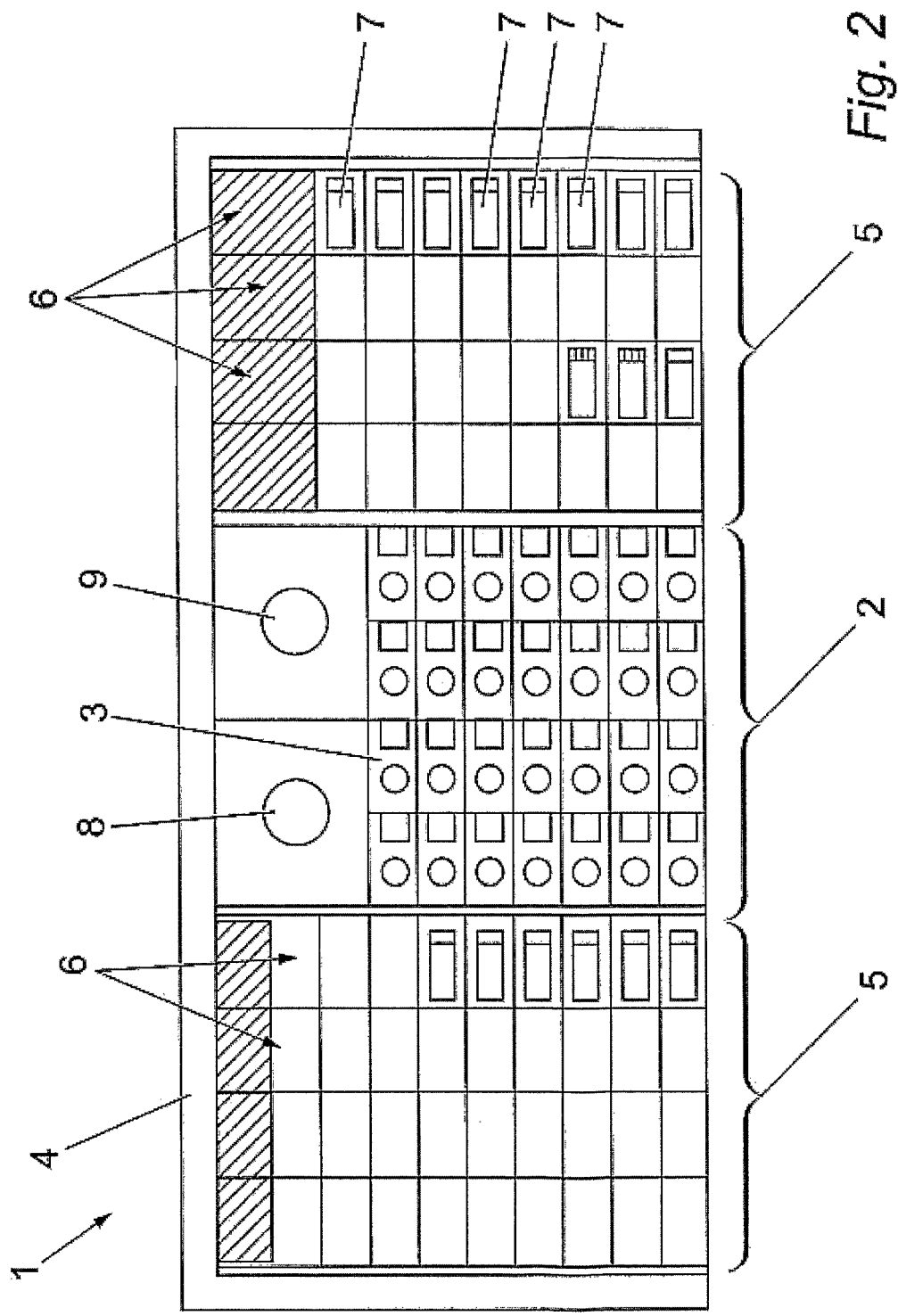
FIG. 2 is a plan view of the apparatus according to the invention.

A preferred embodiment of a staining apparatus in accordance with the present invention is illustrated in FIG. 1. The staining apparatus 1 (FIGS. 1, 2) comprises a frame 4 surrounding at least one reagent station 2 comprising an array of reagent container compartments, each compartment capable of having a reagent container 3 placed therein, and first and second slide sections 5 wherein a number of separate rack assemblies 6 are placed, and where each rack assembly 6 accommodates a number of microscope slides 7 mounted side by side in the rack assembly 6. In the embodiment shown, each rack may hold up to eight slides, but the rack may be designed to hold any suitable number of slides. With eight racks arranged side by side, the shown embodiments may hold up to sixty-four slides 7 each accommodating a biological sample, e.g. a tissue mounted on the upper side of the slide, so that reagent may be applied from above to the sample on each slide.

Also, the reagent container compartments in reagent section 2 may be arranged as a number of separate container racks accommodating a plurality of reagent container compartments. Preferably, the reagent container and the compartment are designed to cooperate in order to avoid a faulty location of a reagent.

In a preferred embodiment the rack assemblies are arranged as drawers in order to ease the access to slides and reagents.

A robot system arranged to provide for movements in X and Y (as well as Z) directions, as indicated by the arrows labeled X, Y and Z in FIG. 1, is arranged above or within the frame 4 of the staining apparatus. The robot system comprises an arm 20 for moving a fluid dispensing device 10 in the form of a probe. The robot arm 20 may therefore position the probe 10 above all reagent containers 3 as well as above all the microscope slides 7, and may further operate the probe 10 to aspirate portions of reagent contained in any of the containers 3, to transfer the portion of reagent and apply it to any of the slides 7 in order to provide a selected staining or treatment of the sample on each slide 7. By use of suitable control means e.g., a computer (not shown) having the appropriate software and input data for the purpose, this staining apparatus 1 is able to automatically stain or treat samples requiring different staining or treatment reagents and processes.

Figure 3:
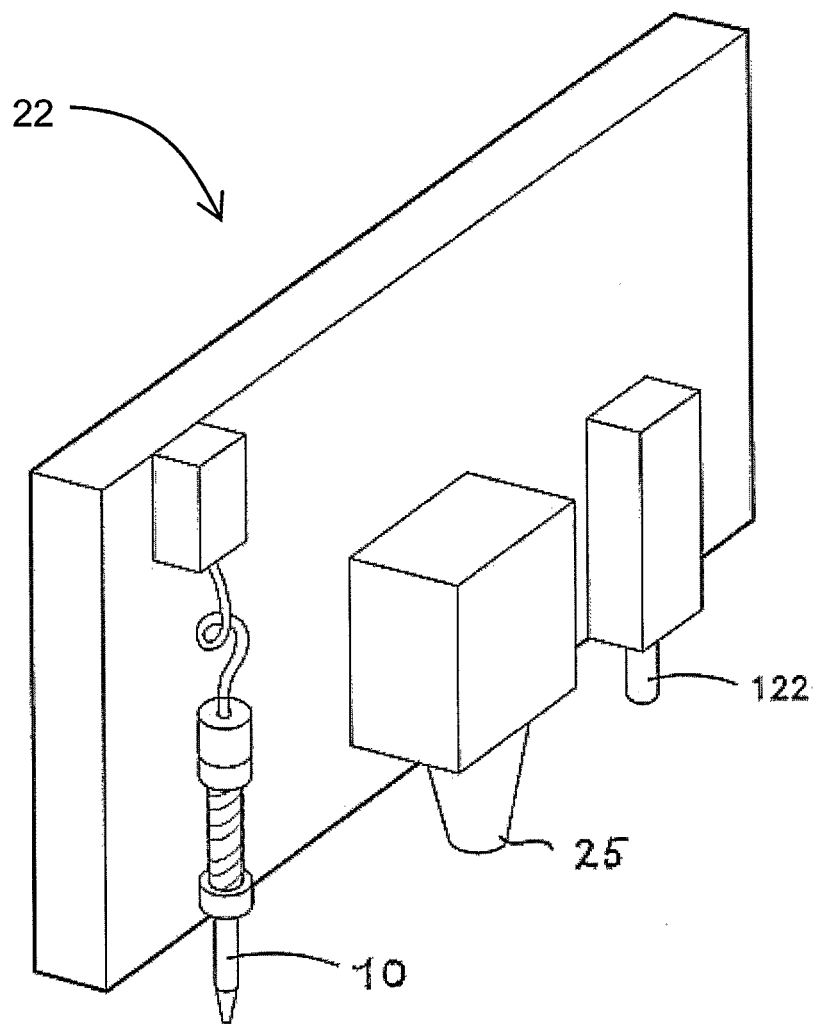
FIG. 3 shows a schematic view of a robotic head with a probe according to the invention mounted thereon.
Figure 4:
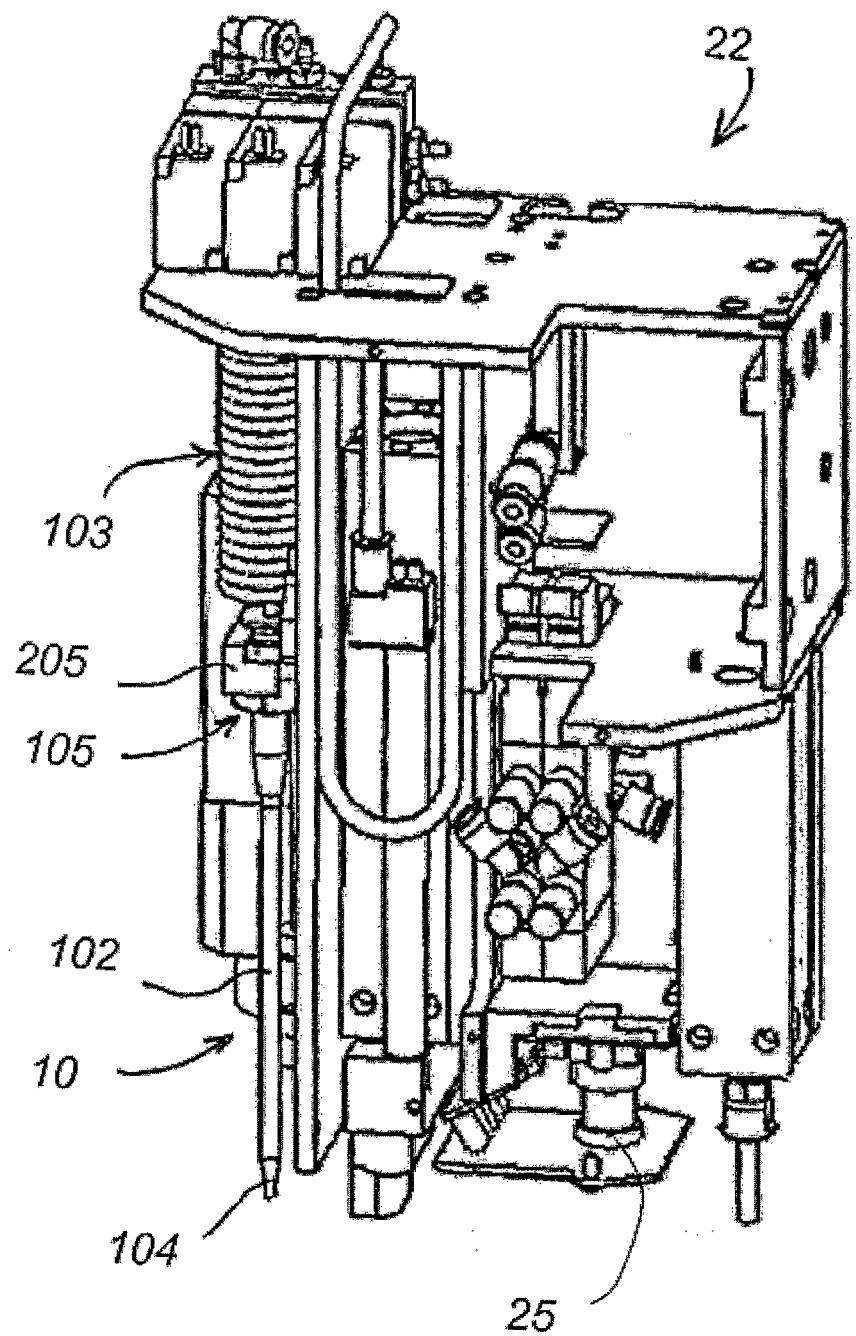
FIG. 4 shows a first view of an embodiment of a robotic head with a probe according to the invention mounted thereon.
Figure 5:
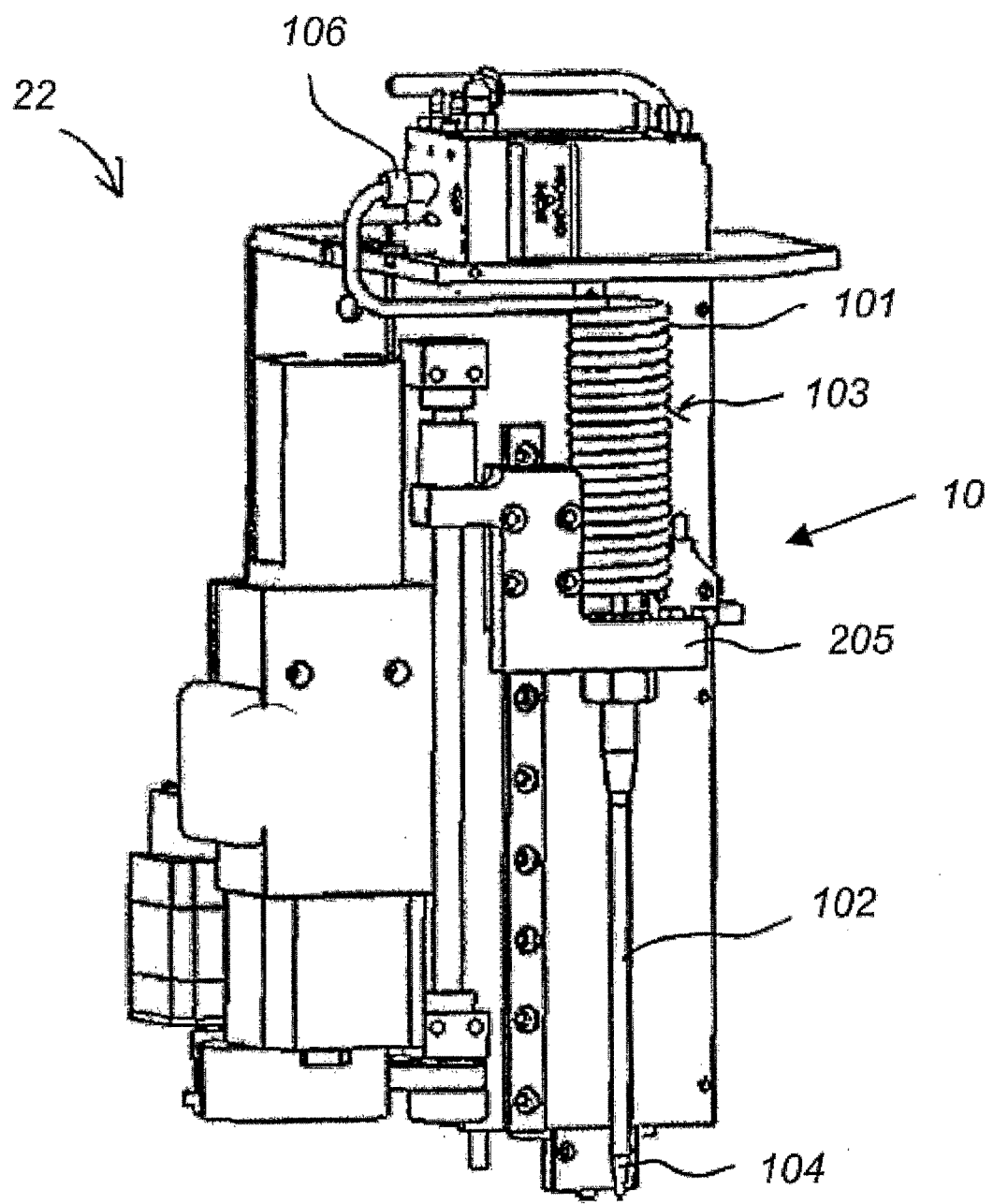
FIG. 5 shows a second view of the robotic head of FIG. 4, viewed perpendicular to the view in FIG. 4.

As shown in FIGS. 1 and 3 and, in more detail, in FIGS. 4 and 5, the probe 10 is mounted in a robotic head 22 and may be manipulated by the robot system. The probe 10 may be raised to an upper position (in a Z direction) where it is clear of the containers 3 underneath the probe 10. Further, the robot comprises means (which may be of well known kind, such as, e.g., a rack and pinion or a hydraulic piston) in the robotic head 22 for lowering the probe 10 in order to insert the probe tip into the content of a selected reagent container or bottle 3 and to aspirate a selected amount of reagent for the selected staining or treatment process.

The robotic head 22 may also be provided with further elements such as a CCD camera 25 pointing downwards. The camera may be utilized to acquire (determine) status information of the slides and the reagent containers and other features of the apparatus in the work area, for example, reading encrypted information provided on a reagent container to determine the reagent type and the reagent location within the system. The robotic head 22 may also be provided with an air nozzle 122 for blowing air onto the slide in order dry the slide or to blow away liquid.

The camera 25 of the robotic head 22 may determine status of the tissue sample carriers, for example, the location of a particular slide or informational indicia, such as encrypted information, that indicate information or the location of information in a database or the like, about the tissue sample presented on the slide or the processing protocol to be performed. In some embodiments, this camera may also be used to locate the sample on the slide, calculate the sample's size, and automatically calculate the most efficient volume of reagent required to process the sample. This capability will allow the stainer 1 to automatically adjust the volumes on the fly without user intervention.

The staining apparatus 1 of the present embodiment may further comprise a probe washing station 8 and a reagent mixer 9, and the robot system may be furthermore arranged to transfer the probe 10 to the washing station 8 as well as to the reagent mixer 9.

Probe

Figure 6:
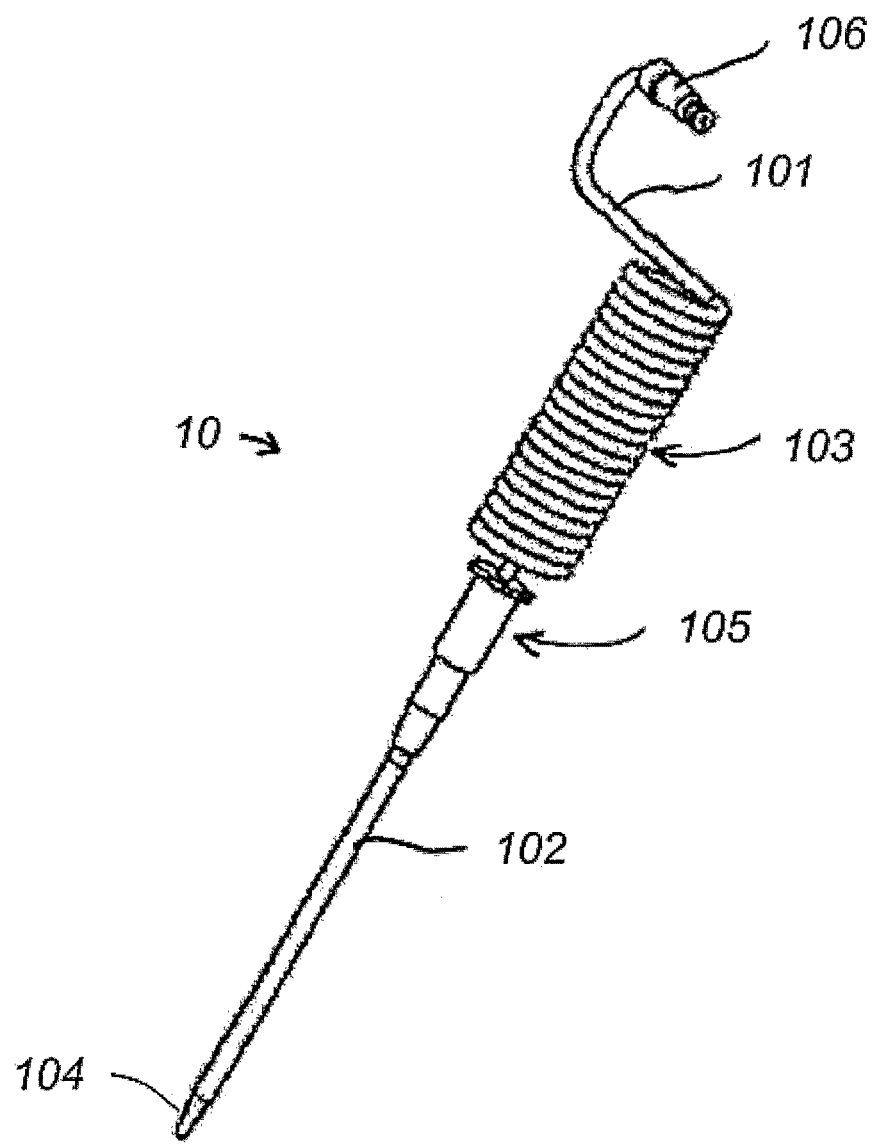
FIG. 6 is a perspective view of a probe according to an embodiment of the invention.
Figure 7:
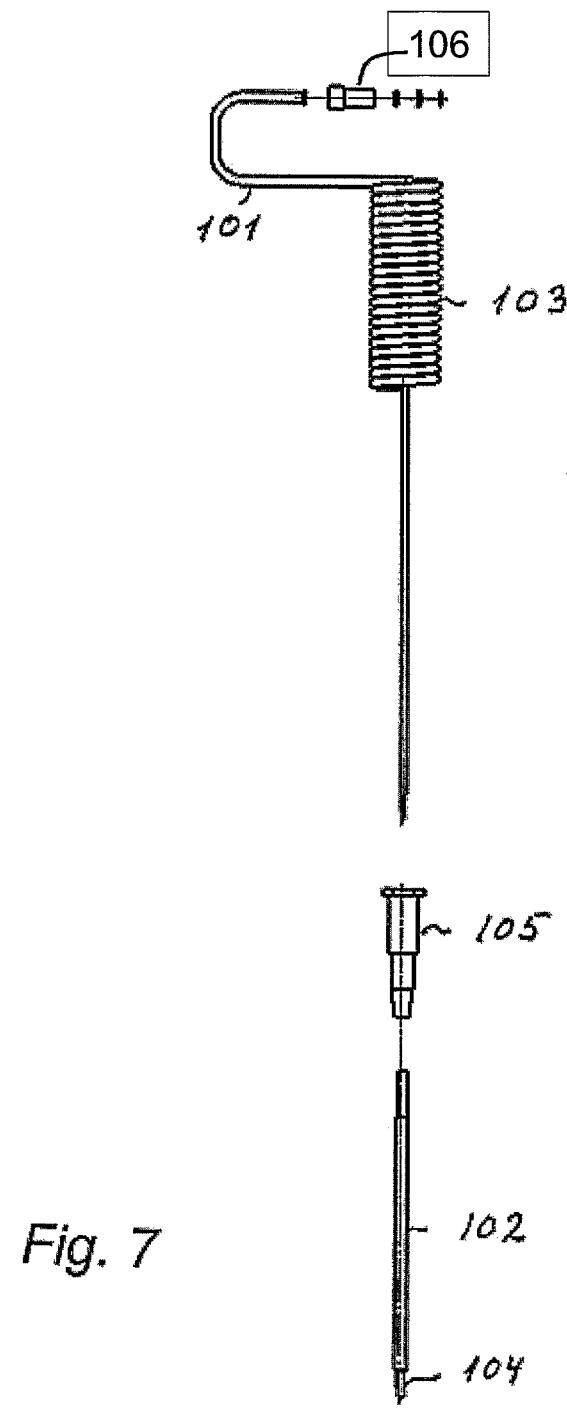
FIG. 7 shows an exploded view of the probe of FIG. 6.

The probe 10 is shown in details in FIGS. 6 and 7. The probe 10 comprises a continuous tubing 101 having a spiral section 103 and a probe member 102 having dispensing end also called probe tip 104, and a mounting end having a fitting 105 for mounting on the robot head 22. Preferably, the probe member 102 is a rigid tube, which may be made from a metal, such as a 300-series stainless steel, coated with a fluoropolymer, e.g. Teflon™. Preferably also the inner tubing is a fluoropolymer, such as Teflon™. The materials for the probe must be able to withstand the fluids to which it will be exposed during the sample processing. Such fluids may include aqueous, alcoholic, acidic, basic and organic solvent liquids.

Preferably, the dispensing end 104 (FIGS. 6-7) is a cone. Preferably, the tubing 101 is arranged as an inner lining of the probe member 102 covering the total inner surface of the probe member 102. The other end of tubing 101 ends in a fitting 106 for connection to a computer controlled pneumatic system, able to provide any desired pressure, enabling the probe to aspirate, with-hold, or dispense predetermined amounts of a fluid. The rigid probe member 102 is mounted with fitting 105 in a holder 205 (FIGS. 4-5) on the robotic head 22.

Preferably, the holder 205 is mounted in a rack and pinion drive and may be moved in a vertical direction raising or lowering the probe relative to the underlying samples.

The spirally wound section 103 of the probe 10 comprises at least one winding and preferably a plurality of windings. It is advantageous in that it may flex as the probe 10 is moved up or down or in any other direction by the robotic head 22. Additionally, this section of tubing in the spirally wound section 103 may provide for a considerably increased internal volume in the tube, so that the probe may hold a relatively large fluid content.

Example: In a preferred embodiment, the inner diameter of the tubing 101 is about 1.5 mm. In one embodiment, the probe shall be able to aspirate a volume of about 2.5 ml. Accordingly, the length of the tubing 101 has to be about 1.5 m. Such length may be accommodated/achieved by including a coil section having about 20 windings and a diameter of about 20 mm providing for about 1260 mm. By adding thereto the length of the rigid probe member and the tubing section from the coil to the fitting 106, a total of 1.5 m of tubing may be obtained. Obviously, the tubing 101 may be designed to accommodate other fluid volumes. The inner diameter of the tubing is determined such that the viscosity of the fluid will secure the fluid in the probe during the movement of the probe from reagent container to a mixer and/or a slide.

Preferably, the robotic head is adapted to lower the probe 10 when it is aligned on top of a selected reagent container. In a preferred embodiment, a reagent container 3 is covered by a cover through which the probe tip 104 may penetrate when so forced by the robotic head. It is advantageous that the probe 10 is capable of automatically gaining entry into the container, as this allows for a "closed" container design, i.e. a reagent container that constantly through all lifetime of use is provided with a protecting cover or septum.

After having pierced the cover or septum covering a reagent container 3, a predetermined amount of the fluid in the container is aspirated into the tubing 101, and the probe 10 is raised. After having aspirated a predetermined volume of fluid into the probe, it may be advantageous to aspirate some air in order to reduce risk of losing a drop of reagent during the robotic transfer of the probe including the fluid to the staining section accommodating the slide for which the reagent is intended. The robotic head moves the probe until it is located directly above the slide, and the probe may be lowered until it is located a predetermined distance above the slide. Then a valve opens for a short moment to the pneumatic device providing a short interval of a pressure dispensing the predetermined volume of reagent to the tissue on the slide.

Alternatively, with the probe raised above a reagent container, an air gap may be created by aspirating air and the probe may be lowered into the reagent container again aspirating a second volume of the same reagent, raised again repeating the aspiration of air and reagent a plurality of times (typically 5-10 times). After having aspirated a plurality of predetermined volumes of reagent for a plurality of predetermined slides, the robotic head moves the probe including fluid and air to the staining section accommodating the slides for which the reagent is intended. This procedure may be very timesaving as the probe is only moved once from the reagent section towards the slide section. It is useful if the same reagent has to be dispensed onto a plurality of slides.

In a further alternative procedure, and, after having aspirated a first fluid and a first air gap into the probe, a second fluid may be aspirated into the probe tubing from another reagent container and a second air gap and so on until reagents for a plurality of slides have been aspirated.

The pneumatic system may control the pressure in the probe tube, providing, for example, a vacuum or a pressure below or above the atmospheric pressure according to control signals, preferably generated by a computer, and, preferably, according to schedules for the treatment of the slides inserted into the stainer. By having "active" vacuum in the tubing of the probe according to the invention, the design of the reagent containers is not critical for ensuring that a predetermined amount of reagent is transferred from the container.

In one embodiment, the probe 10 may be provided with an attached or incorporated fluid level sensor (not shown) for detecting the amount of reagent remaining within a reagent container. Preferably, the fluid level sensor operates by detecting a change in electrical capacitance. Such capacitance level measurement devices are well-known in the art and are commercially available. A capacitor is formed when a level-sensing electrode of the fluid level sensor is inserted to a known depth into a reagent container. The metal rod of the electrode acts as one plate of a capacitor and a reference electrode acts as the other plate. As the level of the reagent in the container rises, the air or gas normally surrounding the electrode is displaced by the reagent's different dielectric constant. The value of the capacitance thus changes because the dielectric between the two plates has changed. This capacitance change is detected electronically and then converted it into an output signal.

With the probe according to the invention, it is possible to provide both precision and accuracy of the aspirated volumes of reagents. This is very important as the staining result may be deteriorated if the applied volumes differ from the recommended sizes, and this could later cause difficulties when analyzing the stained sample in a microscope and might give reason to a faulty diagnosis.

EXAMPLE

Specification for Precision:
  CV<10% at 100 µl and increments of 100 µl to 600 µl dispense volumes.
  20% CV at 20 µl, 40 µl, and 50 µl.
Specification for Accuracy:
  95% at 100 µl and increments of 100 µl to 600 µl dispense volumes.
  20% CV at 20 µl, 40 µl and 50 µl.
  Whenever needed—and typically when a different reagent is to be aspirated and dispensed—the robot system may move the probe to a washing station 8 that is able to clean the probe 10, thereby removing all traces of the preceding reagent from the probe.

Figure 8:
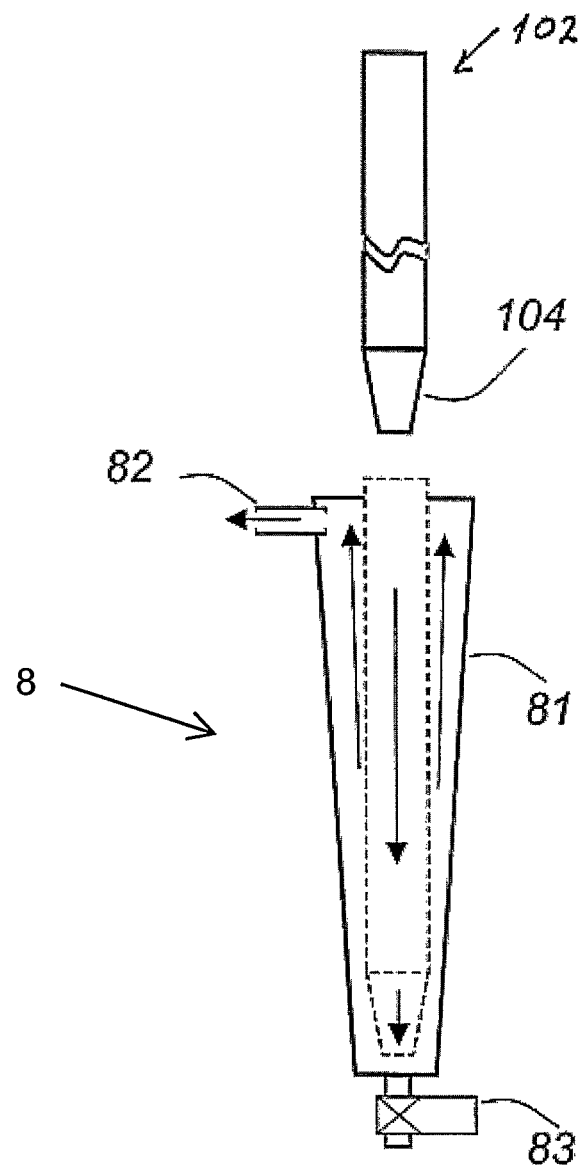
FIG. 8 shows an embodiment of a washing station.
Figure 13:
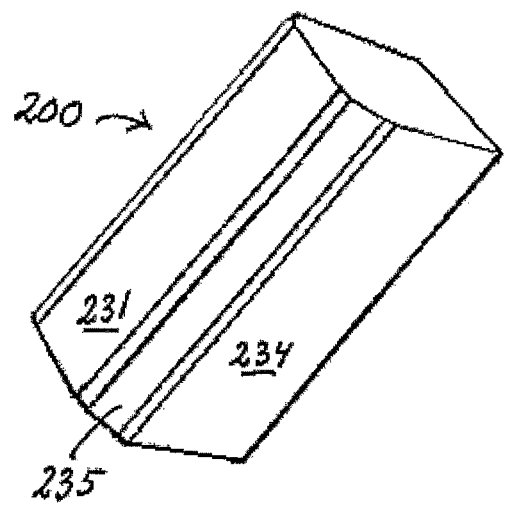
FIG. 13 shows a perspective view of an adapter or covering for accommodation of smaller containers.
Figure 14:
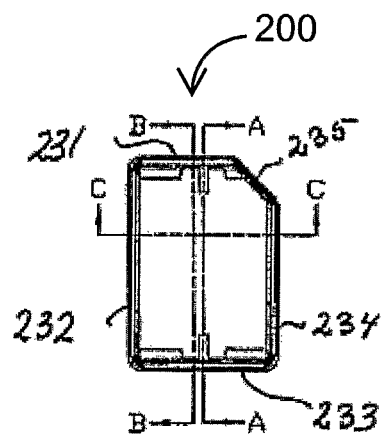
FIG. 14 shows a bottom view of the adapter of FIG. 13.
Figure 15:
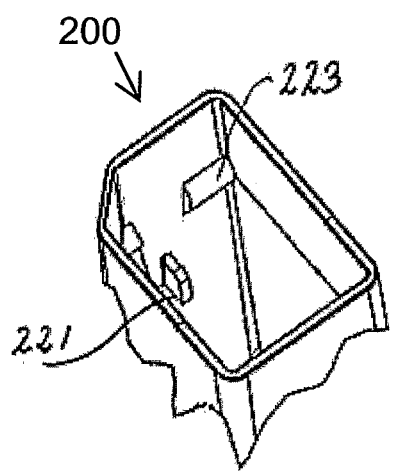
FIG. 15 a perspective view of the adapter of FIG. 13 seen from the top.
Figure 16:
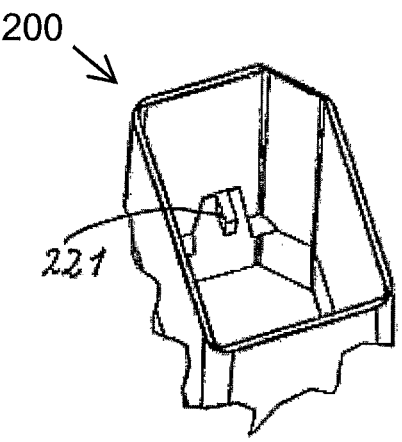
FIG. 16 shows a perspective view of the adapter of FIG. 13, seen from the bottom.

In a preferred embodiment, the washing station 8 (FIG. 8) comprises deep receptacle 81 able to accommodate a length of the rigid probe member 102 at least corresponding to the length which may have been dipped into the reagent. Through valves (not shown), the tubing end with fitting 106 may be connected to a source of at least one wash solution or cleaning fluid, which will pass through the tubing 101 and finally be ejected from the probe tip into the washing receptacle 81. Further, the wash solution or cleaning fluid passes on along the outer surface of the probe 102 and exits the receptacle 81 through an outlet 82 to waste arranged a distance above the bottom and preferably close to the top of the receptacle 81. The receptacle 81 may be emptied by opening a normally-closed bottom valve 83.

In order to dry the probe after the wash, thereby removing any traces of the cleaning fluids, a stream of air may be directed through the probe by connecting the tubing end with the fitting 106 through a valve to an air source.

Reagent Containers:
  In a preferred embodiment, the reagent containers or bottles 3 are designed to fit into the reagent section of the sample processing apparatus, and to cooperate with the design of the probe.

Preferably, the reagent section comprises a plurality of receptacles able to receive a plurality of reagent containers. Preferably, a cross section of these receptacles corresponds to a cross-section of the reagent container. Further, preferably, the cross-section is a non-symmetrical polygon. In a presently preferred embodiment, shown in several of the FIGS. 9-31, the cross-section is a pentagon, and more specifically a pentagon having two sides, and three angles in common with a rectangle. In other words, the preferred cross-section is a rectangle with one corner-section replaced by a slanted/oblique fifth side.

The advantage of the preferred cross section is that the containers can only be arranged in the receptacles with a specific orientation. Also, any other container of different design cannot fit into the receptacle. This may help to avoid problems with faulty supply of reagents. An alternative description of the container shape is that the containers are keyed.

This keying or mating of a container to a receptacle is very important as the top of the container (shown in FIGS. 9, 21, 27, 29) in a preferred embodiment comprises two features: 1) a neck 137 with a cover providing access to the fluid content, and 2) an identification 138 relating to the content of the container, preferably including information specific to the content, such as, e.g., name of chemical substance, date of delivery, date of expiration, and any other relevant information. Alternatively, the identification could be a coded number providing access through a computer to an address comprising such information. It is essential for the automated robotic control of the probe movements that the containers are located precisely in the predetermined positions in the receptacles in the reagent section, so that the probe, when lowered, will hit the cover of the container while, at the same time, the camera (or another sensor device) may read the identification and ensure that the correct reagent will be aspirated.

In a preferred embodiment, the computer system controlling the operation of the robotic system is programmed to start a new sample processing by performing a search of all reagents, identifying the location of the various reagents, preferably using the probe to measure the level of all reagents. In a further preferred embodiment, the computer system is programmed to alert the user if a reagent level is too low to accomplish the staining task for which it is set up. To accomplish this automated operation, it is essential that the reagent containers remain fixedly located in the identified positions. Accordingly, the design of the reagent containers must cooperate tightly with the design of the receptacles in the rack assemblies wherein they are located.

In one embodiment, illustrated in FIGS. 9-12 the container is a 50 ml container 125 having a cross-section that is a rectangle with one corner-section replaced by a slanted/oblique fifth side. The 50 ml container or bottle 125 comprises a bottom 130, five upright sides 131, 132, 133, 134, 135 and a top 136 with a neck 137. In a preferred embodiment, the top, as shown in details in FIG. 10, has identification 138 that is, preferably, a label and that identifies the content of the container.

In view of the fact that some reagents are used in various volumes or even seldom, and still others may have a short shelf-life, needing to be replaced often, there is a need for providing the reagents in containers having different volumes. In order to be able to arrange a plurality of containers having different volumes in the same reagent station with a plurality of identical receptacles, it is preferred to provide an assembly comprising a tube-like covering or shell, called "an adapter", and an internal bottle within the adapter which may be provided in different sizes, having internal volumes of e.g., 1 ml, 2 ml, 5 ml, 10 ml, 15 ml, 20 ml, 25 ml or similar volumes. Generally, the typical reagent volume for an apparatus according to the present invention will be between about 1 ml and 25 ml.

Covering-Adapter:

In a preferred embodiment, the covering is a tube-like element 200 (FIG. 13) having the same outer cylindrical surface as the 50 ml container, i.e., the cross-section is a rectangle with one corner-section replaced by a slanted/oblique fifth side. In order to allow for the computer-controlled automated aspiration of reagents, it is essential that the internal bottles are arranged in a fixed manner inside the tube-like covering 200 enabling the probe to penetrate in a well-defined manner into the fluid content of the bottle. This is achieved by providing the covering and the inner bottles with corresponding projections and indentations respectively and/or vice versa, ensuring a well-defined position of the inner bottle inside the covering. The projections should ensure a correct orientation in all directions. It should not be possible to insert the inner bottle into the adapter 200 in any way other than the intended orientation and position. In a preferred embodiment, this is achieved through the combination of projections and indentations shown in the FIGS. 14-19, relating to the adapter and FIGS. 21-30, relating to containers.

Figure 27:
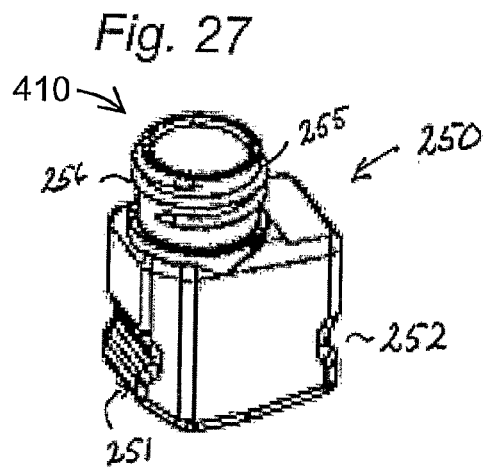
FIG. 27 shows a perspective view of a 10 ml container.
Figure 28:
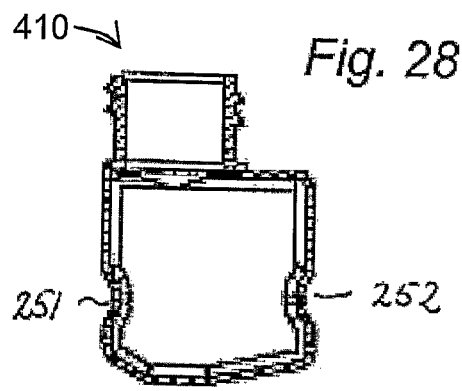
FIG. 28 shows a cross-sectional view of the 10 ml container of FIG. 27.
Figure 29:
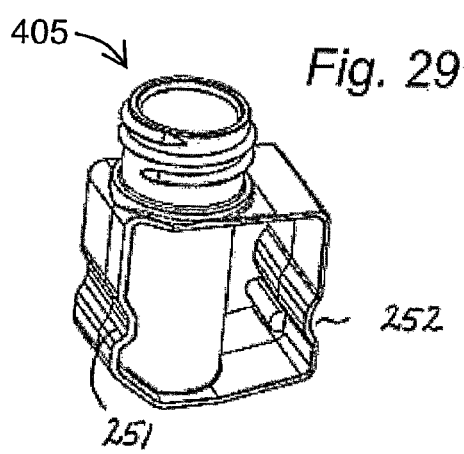
FIG. 29 shows a perspective view of a 5 ml container.
Figure 30:
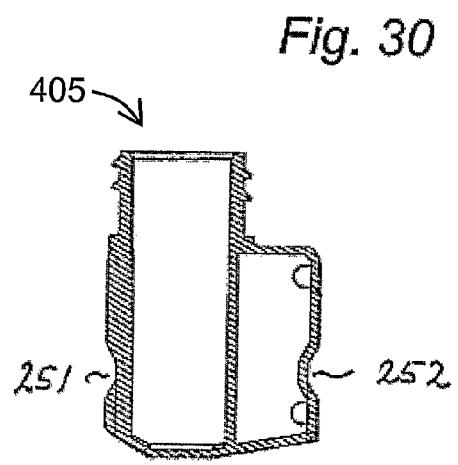
FIG. 30 shows an upright cross-sectional view of the 5 ml container of FIG. 29.
Figure 31:
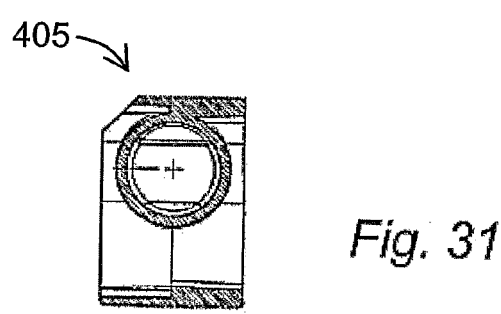
FIG. 31 shows a horizontal cross-sectional view of the 5 ml container of FIG. 29.

Projections 221, 222 in the narrow sides 231, 233 of the adapter 200 will cooperate with the bottom of an inner bottle such as a 10 ml bottle 410 shown in FIGS. 27-28 or a 5 ml bottle shown in FIGS. 29-31. Further projections 223, 224, in the same sides cooperate with indentations 251, 252 in the bottle. In this manner, the bottle will remain in the fixed position in the adapter 200, even when exposed to the pressure from a probe being inserted through a top cap. A 25 ml bottle 250 shown in FIGS. 21-26 has further indentations 261, 262 allowing this bottle to pass by the projections 221, 222.

Figure 32:
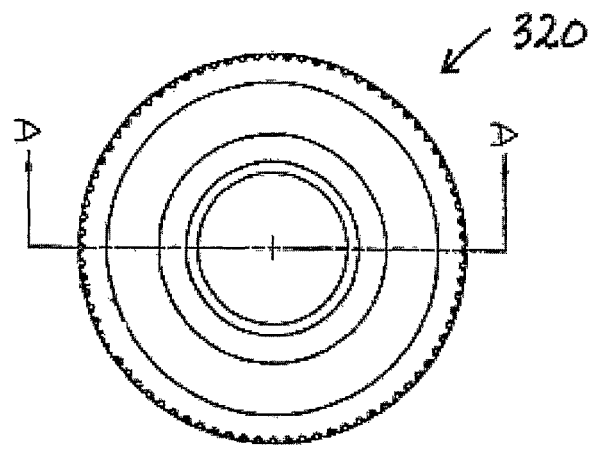
FIG. 32 shows a top view of a cap for a container.
Figure 33:
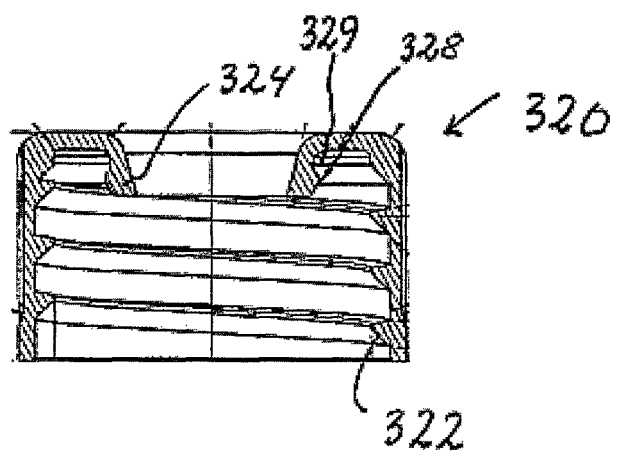
FIG. 33 shows a cross-sectional view of the cap of FIG. 32.

In a preferred embodiment, the 10 ml inner bottle 410 (FIGS. 27-28) and the 5 ml bottle 405 (FIGS. 29-30) have a neck 255 with an external thread 256 and a corresponding cap 320 (shown in FIGS. 32-23) with an internal thread 322, providing a closure for the bottle 410 or the bottle 405. The 5 ml bottle 405 has identical external dimensions and shape as the 10 ml bottle 410 but has a different internal volume. The cap 320 may comprise a circular opening through which the probe may aspirate the fluid content in the bottle. In this manner, no operator has to unscrew a cap in order provide access to the content. The probe may simply reach the fluid content when the probe is lowered by the robotic system until the probe makes contact with the fluid. Preferably, a fluid level sensor of the probe is in electrical connection with electronic circuits enabling a determination of the fluid level in the container. Alternatively and in some embodiments, a second database method of reagent volume tracking may be used instead of or in conjunction with previously detailed electronic method. The database method employs the use of a database to track the usage of a reagent removed by the probe from a specific container and calculates the remaining available volume.

Figure 34:
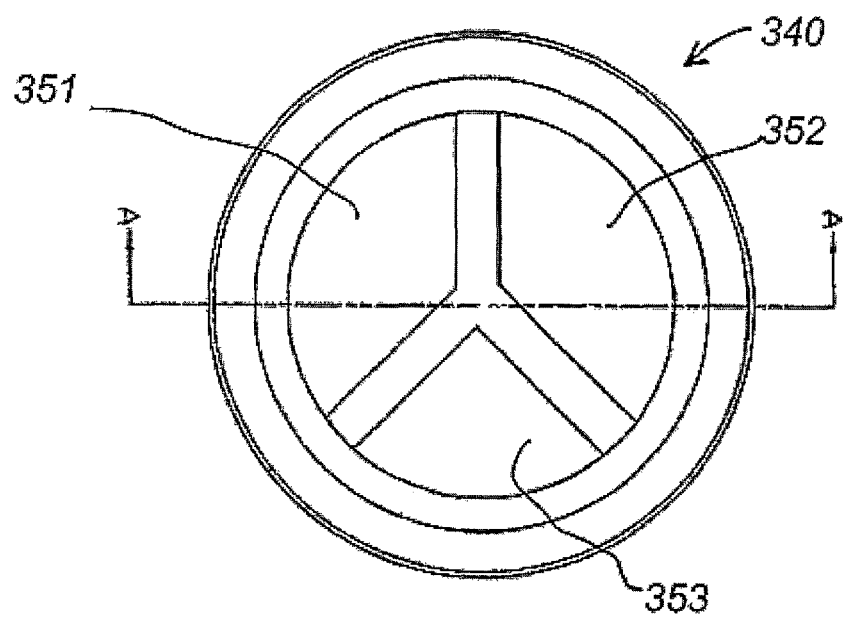
FIG. 34 shows a septum.
Figure 35:
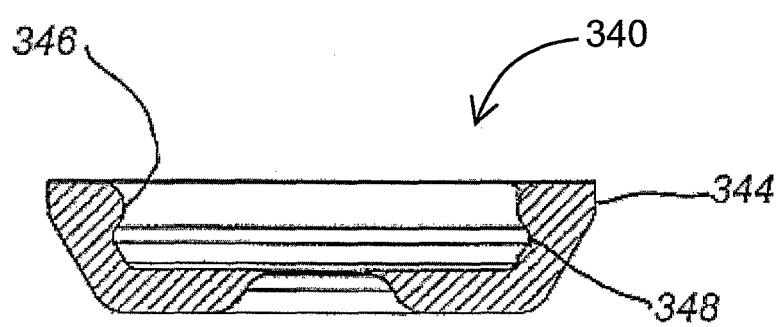
FIG. 35 shows a cross-sectional view of the septum along the line A-A in FIG. 34.

However, in order to protect the reagent fluids from contamination as well as evaporation, it is highly desirable to provide tight closures for the bottles. To this end, the circular opening in the cap 320 has a skirt 324 with a peripheral edge 326 including a peripheral outwardly projecting rim or lip 328 and a peripheral/surrounding indentation or groove 329 able to cooperate with and fixate a corresponding septum 340 (FIGS. 34-35) comprising a flexible material such as polypropylene. The corresponding septum 340 has an upward skirt 344 with an inwardly projecting rim or lip 346 and groove/indentation 348, able to cooperate with the indentation 329 and rim/lip 328 inside the cap 320. When the cap 320 is secured to the bottle neck 255, the upper end of the neck will support and force the lip 346 to stay locked in the groove 329.

Preferably, the septum 340 (FIGS. 34-35) comprises a plurality of sectors or flaps 351, 352, 353, such as 2, 3 or 4 sectors, which are free to flex upwards or downwards thereby allowing a probe to penetrate the septum. After aspiration of the predetermined amount of fluid, the probe is raised again, thereby being retracted from the reagent bottle. During retraction of the probe, the flaps will wipe off the reagent from the outer surface of the probe. After retraction of the probe, the flaps return to their original position forming an almost tight closure inside the cap on top of the bottle. This septum has several advantages: Evaporation of reagent is reduced, and the wiping action of the flaps saves reagent from being carried away on the outer surface of the probe when the probe is raised for movement to the slide section.

Preferred Modes of Operation:

An operator enters relevant input data—relating to a requested processing of a number of slides, which are to be processed, —on a computer connected to the control system controlling one or more sample processing apparatus, such as stainers. When a stainer is vacant or a requested number of slide positions in a rack in a drawer of a stainer are vacant the slides are loaded into the vacant position.

Having the appropriate input data, the control means of the apparatus operates the robot arm to commence a processing of the slides. When a reagent is needed for a staining or treatment the robot moves the probe to a first reagent container 3, into which the probe tip 12 is inserted into the reagent, and reagent is aspirated into the probe 10 in an amount corresponding to the number of samples to be stained or treated, in accordance with the input data provided to the control means.

The probe 10 is subsequently, in a first operating mode, moved by the robot arm 20 towards the slide rack assembly 6 within a slide section 5 in which the slides 7 are mounted. The slides 7 are situated with the surface horizontally oriented and the probe 10 releases the required amount of reagent onto the appropriate slides in accordance with the input data. Alternatively, the probe 10, in a second operating mode, may be moved by the robot arm 20 towards the reagent mixer 9 where it releases the reagent into a cup portion of the reagent mixer 9, and is subsequently moved to the probe washing station 8, where the probe 10 is washed and dried. The robot arm 20 moves the newly cleaned probe 10 to a second selected reagent container 3 for collecting a selected amount of reagent from the second container 3, and the probe 10 is thereafter, by means of the robot arm, moved to the reagent mixer 9, where the reagent in the probe 10 is dispensed into the cup of the mixer containing the first selected reagent. This second operating mode can, according to the invention, be commenced several times if more than two reagents are to be mixed for a specific staining or treatment process. After thorough mixing, the required amount of mixed reagents are withdrawn from the reagent mixer 9 by the probe 10 and dispensed onto the appropriate slides in accordance with the input data.

Subsequently, the robot arm with the probe 10 is directed to the washing station 8, and the probe 10 is washed and dried. Thereafter, the process in accordance with the first or the second operating mode may be repeated or continued with new reagents or reagent mixtures according to processing steps defined in a protocol for the treatment of the slides.

According to a preferred method, the probe tubing 101, having aspirated a predefined volume of a first reagent, may be removed from the first reagent container, aspirate a predetermined amount of air, forming an air gap or bubble inside the tubing, and then enter into a second reagent container and aspirate the second reagent. The air bubble separates the two reagents and the meniscus of the bubble acts as a wiper within the inner tubing wall to eliminate cross contamination between these two distinct fluids. In similar manner, a plurality of different reagents may be aspirated and separated by air during a single period in which the robotic head 22 locates the probe 10 over the reagent section of the stainer. Afterwards, the computer controlled robotic head 22 can move the probe to the section 5 with the slides 7, and during the following period, dispense one or more reagents on a single or a plurality of slides, possibly requiring different reagents. Aspirating a plurality of volumes for a plurality of microscope slides is very time-saving, supporting a high through-put of the apparatus, as the probe only moves once from the reagent section 2 to the staining section with the slides, yet dispensing a plurality of reagent volumes on a plurality of slides.

Returning to the aspect of monitoring or capturing information, an embodiment of the system may be designed to monitor replenishable supply information, such as the status of buffers, reagents, stains or the like. By monitoring for a potential need for replenishable supplies, the system may remove at least one possibility for human error. Significantly, the system may also act to automatically notify any number of people relative to the information monitored. With respect to replenishable supply information, the system may notify a user, an operator, an administrator, or even a supplier of an actual, potential, or impending need to replenish supplies. As such the system may be considered as including an automatic notice element, or the like.

The invention is described above with reference to a preferred embodiment. However, it is realized that variants may be provided without departing from the scope of the invention as defined in the accompanying claims.

List Of Components And Reference Numbers
staining apparatus—1
reagent station (section)—2
reagent container (bottle/vial)—3
frame—4
first and second slide sections (staining sections)—5
rack assemblies (rack systems)—6
microscope slides or carrier elements (for biological samples)—7
probe washing station—8
receptacle—81 (in 8)
outlet—82
bottom valve—83
reagent mixer—9
fluid (reagent) dispensing device or probe—10
robot arm—20
robotic head—22
CCD camera—25
flexible tube (continuous probe tubing element)—101
probe member—102
spirally wound section (coil, winding)—103
nozzle end, aspirating and dispensing end—104
probe mounting end—105
connection fitting—106
air nozzle—122
holding means, holder—205
pneumatic pressure regulation device (not shown)
50 ml container bottle—125
identification (label)—156
bottom 130; sides—131, 132, 133, 134, 135
top 136; neck 137; label 138.
Covering, shell—200
sides—231, 232, 233, 234, 235
projections—221, 222, 223, 224
25 ml container (bottle/vial)—250
10 ml container (bottle/vial)—410
5 ml container (bottle/vial)—405
container body indentations—251, 252
neck, upper opening—255
external thread—256
cap—320
internal thread—322
skirt 324; edge 326; rim/lip 328
groove/indentation—329
septum—340; upward skirt 344
projection/rim/lip—346
indentation/groove—348
flaps—351-353

What is claimed is:

1. A reagent delivery system in an apparatus for processing biological samples arranged on carrier elements, the apparatus comprising a stationary reagent section having one or more reagent containers and a stationary staining section in which at least one carrier element is arranged, comprising: a probe for aspirating a portion of reagent from a reagent container in order to dispense a predetermined amount on a predetermined carrier element;
and a probe handling device for handling the probe, wherein the probe comprises a continuous probe tubing extending through a rigid probe member and providing fluid communication from a dispensing end of said probe member to a pneumatic pressure regulation device and wherein the rigid probe member is adapted for cooperation with the closure of the reagent container, wherein the continuous probe tubing is provided with a spirally wound probe tubing section.

2. A reagent delivery system according to claim 1, wherein the rigid probe member is arranged to cooperate with at least one reagent container in such manner that the probe may penetrate an opening covered by a septum, aspirate reagent, and withdraw from the container, and wherein the septum is adapted so as to become substantially closed after withdrawal.

3. A reagent delivery system according to claim 2, wherein the septum comprises a plurality of sectors or flaps which are free to flex upwards or downwards.

4. A reagent delivery system according to claim 2, wherein the septum comprises a plurality of sectors or flaps, which, originally, are connected by lines of weakness such that the lines of weakness will break the first time a probe is inserted into the reagent container, and, afterwards, are free to flex upwards or downwards.

5. A reagent delivery system according to claim 1, wherein the dispensing end of the probe comprises a conical shape.

6. A reagent delivery system according to claim 1, further comprising: an identification on a reagent container;
a sensor element on the probe handling device that is able to acquire information from the identification; and
a computer electrically coupled to the sensor element and receiving the information.

7. A staining apparatus for automated processing of biological samples arranged on carrier elements, comprising: a reagent section comprising one or more reagent containers;
a staining section in which at least one carrier element is arranged;
a reagent dispensing device for dispensing a portion of reagent onto a predetermined carrier element; and
a handling device for handling said reagent dispensing device, wherein the reagent dispensing device comprises a continuous probe tubing extending through a rigid probe member and providing fluid communication from a dispensing end of said probe member to a pneumatic pressure regulation device, wherein the continuous probe tubing is provided with a spirally wound probe tubing section.

8. A staining apparatus according to claim 7, wherein the pneumatic pressure regulation device includes a vacuum source with which the tubing may communicate via a valve device.

9. A staining apparatus according to claim 8, wherein said valve device is operable to provide a predetermined pressure in the tubing for aspirating or dispensing a predetermined amount of reagent in the dispensing end of the tubing.

10. A staining apparatus according to claim 8, wherein said valve device is adapted to provide a connection to a fluid source providing a wash solution or cleaning fluid for washing and or rinsing the probe tubing.

11. A staining apparatus according to claim 10, wherein said washing fluid is selectable from a plurality of fluids according to the tube cleaning requirements.

12. A staining apparatus according to claim 7, wherein the handling device comprises: a holder for holding the probe member; and
a robotic motion system for moving the reagent dispensing device between predetermined locations relative to the carrier element and the reagent containers.

13. A staining apparatus according to claim 7, wherein the internal diameter of the tubing is between 1.0 mm and 2.0 mm.

14. A staining apparatus according to claim 7, wherein the length of the tubing is between 0.5 m and 2.5 m.

15. A staining apparatus according to claim 7, wherein the spirally wound probe tubing section is a coiled section.

16. A staining apparatus according to claim 15, wherein the coiled section comprises between 5 and 30 windings.

17. A staining apparatus according to claim 15, wherein the washing station comprises: a receptacle able to accommodate a substantial portion of the dispensing end of the probe; and an outlet to waste.

18. A staining apparatus according to claim 17 wherein the outlet to the waste is located a distance above the bottom of the receptacle so that the wash fluid ejected from the dispensing end of the probe will wash the outer surface of the dispensing end of the probe before the wash fluid is drained to waste.

19. A staining apparatus according to claim 7, further including a washing station for cleaning the reagent-dispensing device.

20. A staining apparatus according to claim 7, wherein the reagent section comprises a compartment for a reagent container wherein the cross-section of the compartment cooperates with the cross-section of the container.

21. A staining apparatus according to claim 20, wherein the cross-section is an unsymmetrical polygon.

22. A staining apparatus according to claim 21, wherein a top wall of a reagent container is provided with a label comprising identifying information and wherein the robot head further comprises an optical sensor, able to provide the information on the label to a computer system.

23. A staining apparatus according to claim 22, wherein the computer system is connected to a plurality of staining apparatuses, wherein the computer system uses the reagent dispensing device to detect the level of reagent fluid in each reagent container, wherein the computer system maintains information about the available amount of reagent in the reagent containers in the plurality of staining apparatuses.

24. A staining apparatus according to claim 21, wherein the computer system will issue an order for a new delivery of the reagent if the level is below a predetermined limit.

25. A staining apparatus according to claim 7, wherein an electrically conducting member of the reagent dispensing device is connected to an electronic circuit adapted for capacitive level sensing.

26. A reagent dispensing device for use in a staining apparatus for processing of biological samples arranged on carrier elements, said device comprising: a probe member having an aspirating and dispensing end, through which reagent may be aspirated and dispensed; and a continuous probe tubing provided inside the probe member, said tubing extending from the aspirating and dispensing end through the entire probe member to a pneumatic pressure regulation device, wherein the continuous tubing is provided with a spirally wound probe tubing section.

27. A reagent dispensing device according to claim 26, wherein the internal diameter of the tubing is between 1.0 mm and 2.0 mm.

28. A reagent dispensing device according to claim 26, wherein the length of the tubing is between 0.5 m and 2.5 m.

29. A reagent dispensing device according to claim 26, wherein the spirally wound probe tubing section is a coiled section.

30. A reagent dispensing device according to claim 29, wherein the coiled section comprises between 5 and 30 windings.

31. A reagent dispensing device according to claim 26, wherein a mounting end of the probe member includes a fitting for mounting the probe member to a probe handling device.

* * * * *